US008741589B2

(12) United States Patent
Hellerstein

(10) Patent No.: US 8,741,589 B2
(45) Date of Patent: *Jun. 3, 2014

(54) MONITORING TWO DIMENSIONS OF DIABETES PATHOGENESIS

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 804 days.

This patent is subject to a terminal disclaimer.

(21) Appl. No.: 11/451,735

(22) Filed: Jun. 12, 2006

(65) Prior Publication Data

US 2006/0280682 A1 Dec. 14, 2006

Related U.S. Application Data

(60) Provisional application No. 60/689,612, filed on Jun. 10, 2005.

(51) Int. Cl.
*C12Q 1/54* (2006.01)

(52) U.S. Cl.
USPC .............................. 435/14; 424/9.1; 424/9.2

(58) Field of Classification Search
None
See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zolotarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami et al. |
| 6,329,208 B1 | 12/2001 | Jones et al. |
| 6,355,416 B1 | 3/2002 | Abramson |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 | 10/2004 | Hellerstein |
| 6,835,927 B2 | 12/2004 | Becker et al. |
| 6,849,396 B2 | 2/2005 | Schneider |
| 6,872,575 B2 | 3/2005 | Regnier |

(Continued)

FOREIGN PATENT DOCUMENTS

| | | |
|---|---|---|
| CA | 2494715 A1 | 2/2004 |
| EP | 0826377 | 11/2002 |

(Continued)

OTHER PUBLICATIONS

Linn et al. (2000) Diabetologia 43: 1257-1265.*
Jones et al. (2001) Am. J. Physiol. Endocrinal. Metab. 281: E848-856.*
International Search Report and Written Opinion mailed Oct. 11, 2007, for PCT Application No. PCT/US05/05660 filed Feb. 22, 2005, 11 pages.
U.S. Office Action mailed on Oct. 5, 2007, for U.S. Appl. No. 11/094,387, filed Mar. 29, 2005, 22 pages.
Jones, J. G. (2001). "An Integrated 2H and 13C NMR Study of Gluconeogenesis and TCA Cycle Flux in Humans," *American Journal of Physiology-Endocrinology and Metabolism* 281:E848-856.

(Continued)

*Primary Examiner* — Lisa J Hobbs
(74) *Attorney, Agent, or Firm* — Morrison & Foerster LLP

(57) ABSTRACT

Provided are methods for determining concurrently with a simple, minimally invasive test, the adequacy of pancreatic beta-cell compensation and/or the presence of tissue insulin resistance in a subject human or an experimental animal. The methods allow for the determination of a subject's or experimental animal's susceptibility to developing type 2 diabetes mellitus (DM2) or to progression to more advanced forms of DM2. Among other uses, the methods allow for diagnostic classification of subjects for decisions regarding therapeutic interventions, clinical differentiation between type 1 DM and DM2, clinical monitoring of treatments intended to reduce risk of developing DM2 in non-diabetic subjects, clinical monitoring of agents intended to improve existing DM2 and to prevent progression of DM2, clinical development and testing of new compounds, candidate agents, or candidate therapies for preventing progression to DM2 or disease progression in existing DM2, and preclinical screening of candidate agents or candidate therapies in experimental animals to identify and characterize agents having insulin-sensitizing properties, pancreatic stimulatory or regenerative properties or other desirable actions.

8 Claims, 16 Drawing Sheets

(56) References Cited

U.S. PATENT DOCUMENTS

| | | | |
|---|---|---|---|
| 6,887,712 B1 | 5/2005 | Medford et al. | |
| 6,902,719 B2 | 6/2005 | Wagner | |
| 6,906,320 B2 | 6/2005 | Sachs et al. | |
| 7,001,587 B2 | 2/2006 | Hellerstein | |
| 7,022,834 B2 | 4/2006 | Hellerstein | |
| 7,048,907 B2 | 5/2006 | Groman et al. | |
| 7,057,168 B2 | 6/2006 | Miller et al. | |
| 7,084,396 B2 | 8/2006 | Schneider | |
| 7,256,047 B2 | 8/2007 | Malloy et al. | |
| 7,449,171 B2 | 11/2008 | Hellerstein | |
| 7,504,233 B2 | 3/2009 | Hellerstein | |
| 7,910,323 B2 | 3/2011 | Hellerstein | |
| 8,005,623 B2 | 8/2011 | Hellerstein | |
| 8,021,644 B2 | 9/2011 | Hellerstein | |
| 8,129,335 B2 | 3/2012 | Hellerstein | |
| 2003/0068634 A1 | 4/2003 | Hellerstein | |
| 2003/0119069 A1 | 6/2003 | Schneider et al. | |
| 2003/0133871 A1 | 7/2003 | Hellerstein | |
| 2003/0148533 A1 | 8/2003 | Malloy et al. | |
| 2003/0180710 A1 | 9/2003 | Lee et al. | |
| 2003/0180800 A1* | 9/2003 | Lee et al. | 435/7.1 |
| 2003/0211036 A1 | 11/2003 | Degani et al. | |
| 2003/0224420 A1 | 12/2003 | Hellerstein et al. | |
| 2003/0228259 A1 | 12/2003 | Hellerstein | |
| 2004/0081994 A1* | 4/2004 | Hellerstein | 435/6 |
| 2004/0115131 A1 | 6/2004 | Hellerstein | |
| 2004/0121305 A1 | 6/2004 | Wiegand et al. | |
| 2004/0152994 A1 | 8/2004 | Meier-Augenstein | |
| 2004/0191916 A1 | 9/2004 | Gross et al. | |
| 2004/0253647 A1 | 12/2004 | Mathews et al. | |
| 2005/0003375 A1 | 1/2005 | Franza et al. | |
| 2005/0014181 A1 | 1/2005 | Galis et al. | |
| 2005/0019251 A1 | 1/2005 | Hellerstein | |
| 2005/0092910 A1 | 5/2005 | Geromanos et al. | |
| 2005/0118724 A1 | 6/2005 | Bateman et al. | |
| 2005/0147558 A1 | 7/2005 | Hellerstein | |
| 2005/0153346 A1 | 7/2005 | Schneider | |
| 2005/0175982 A1 | 8/2005 | Iwatani et al. | |
| 2005/0180949 A1* | 8/2005 | Emtage et al. | 424/85.1 |
| 2005/0201937 A1 | 9/2005 | Hellerstein | |
| 2005/0202406 A1 | 9/2005 | Hellerstein | |
| 2005/0221278 A1 | 10/2005 | Iwatani et al. | |
| 2005/0238577 A1 | 10/2005 | Hellerstein | |
| 2005/0238581 A1* | 10/2005 | Kurland et al. | 424/9.2 |
| 2005/0249664 A1 | 11/2005 | Hellerstein | |
| 2005/0255509 A1 | 11/2005 | Hellerstein et al. | |
| 2005/0281745 A1 | 12/2005 | Lee et al. | |
| 2006/0008796 A1 | 1/2006 | Hellerstein | |
| 2006/0020440 A1* | 1/2006 | Hellerstein | 703/11 |
| 2006/0029549 A1 | 2/2006 | Hellerstein | |
| 2006/0094057 A1 | 5/2006 | Hellerstein | |
| 2006/0100903 A1 | 5/2006 | Lee et al. | |
| 2006/0105322 A1 | 5/2006 | Iwatani et al. | |
| 2006/0105339 A1 | 5/2006 | Hellerstein | |
| 2006/0120961 A1 | 6/2006 | Schneider et al. | |
| 2006/0204439 A1 | 9/2006 | Hellerstein | |
| 2006/0251576 A1 | 11/2006 | Hellerstein | |
| 2006/0280682 A1 | 12/2006 | Hellerstein | |
| 2007/0248540 A1 | 10/2007 | Hellerstein | |
| 2008/0003179 A1 | 1/2008 | Hellerstein | |
| 2009/0041661 A1 | 2/2009 | Hellerstein | |

FOREIGN PATENT DOCUMENTS

| | | |
|---|---|---|
| JP | 2001-211782 A | 8/2001 |
| JP | 2003-79270 A | 3/2003 |
| SU | 968036 | 10/1982 |
| WO | WO-90/11371 | 10/1990 |
| WO | WO-93/20800 | 10/1993 |
| WO | WO-93/25705 | 12/1993 |
| WO | WO-95/13096 | 5/1995 |
| WO | WO-98/51820 | 11/1998 |
| WO | 00/12535 A2 | 3/2000 |
| WO | WO-00/13025 | 3/2000 |
| WO | WO-00/63683 | 10/2000 |
| WO | WO-01/80715 | 11/2001 |
| WO | WO-01/84143 | 11/2001 |
| WO | WO-03/061479 | 7/2003 |
| WO | WO-03/068919 | 8/2003 |
| WO | WO-03/087314 | 10/2003 |
| WO | WO-2004/003493 | 1/2004 |
| WO | 2004/016156 A2 | 2/2004 |
| WO | WO-2004/011426 | 2/2004 |
| WO | WO-2004/021863 | 3/2004 |
| WO | WO-2004/024941 | 3/2004 |
| WO | WO-2004/025270 | 3/2004 |
| WO | WO-2004/042360 | 5/2004 |
| WO | 2004/016156 A3 | 6/2004 |
| WO | WO-2005/009597 | 2/2005 |
| WO | WO-2005/015155 | 2/2005 |
| WO | WO-2005/033652 | 4/2005 |
| WO | WO-2006050130 A2 | 5/2006 |
| WO | WO-2006081521 A2 | 8/2006 |
| WO | WO-2006107814 A2 | 10/2006 |

OTHER PUBLICATIONS

Turner, S. M. (2006). "Stable Isotopes, Mass Spectrometry, and Molecular Fluxes: Applications to Toxicology," *Journal of Pharmacological and Toxicological Methods* 53:75-85.

Turner, S. M. et al. (2005). "Emerging Applications of Kinetic Biomarkers in Preclinical and Clinical Drug Development," *Current Opinion in Drug Discovery & Development* 8(1): 115-126.

U.S. Office Action mailed on Dec. 14, 2007, for U.S. Appl. No. 10/701,990, filed Nov. 4, 2003, 8 pages.

Zhang, B.-L. et al. (2006). "Deuterium NMR Study of the Origin of Hydrogen in Fatty Acids Produced In Vivo in by Chicken," *European Journal of Lipid Science and Technology* 108:125-133.

Boros, L. G. et al. (2001). "Genistein Inhibits Nonoxidative Ribose Synthesis in MIA Pancreatic Adenocarcinoma Cells: A New Mechanism of Controlling Tumor Growth," *Pancreas* 22(1):1-7.

Boros, L. G. et al. (Mar. 2002). "Metabolic Profiling of Cell Growth and Death in Cancer: Applications in Drug Discovery," *Drug Discovery Today* 7(6):364-372.

Supplementary European Search Report mailed Sep. 19, 2008, for EP Application No. 05733311.4 filed Feb. 2, 2005, 9 pages.

Maric, D. et al. (2000). "Functional Ionotropic Glutamate Receptors Emerge During Terminal Cell Division and Early Neuronal Differentiation of Rat Neuroepithelial Cells," *Journal of Neuroscience Research* 61(6):652-662.

U.S. Appl. No. 11/796,438, filed Apr. 26, 2007 for Hellerstein.

U.S. Office Action mailed on Jul. 21, 2006, for U.S. Appl. No. 10/963,967, filed Oct. 12, 2004, 7 pages.

U.S. Office Action mailed on Jan. 11, 2007, for U.S. Appl. No. 10/963,967, filed Oct. 12, 2004, 6 pages.

U.S. Office Action mailed on Mar. 5, 2007, for U.S. Appl. No. 10/366,125, filed Feb. 12, 2003, 6 pages.

U.S. Office Action mailed on Jun. 26, 2006, for U.S. Appl. No. 10/366,125, filed Feb. 12, 2003, 11 pages.

U.S. Office Action mailed on Oct. 18, 2005, for U.S. Appl. No. 10/366,125, filed Feb. 12, 2003, 29 pages.

U.S. Office Action mailed on Mar. 30, 2006, for U.S. Appl. No. 10/664,513, filed Sep. 16, 2003, 15 pages.

U.S. Office Action mailed on Oct. 20, 2005, for U.S. Appl. No. 10/664,513, filed Sep. 16, 2003, 12 pages.

U.S. Office Action mailed on Aug. 8, 2006, for U.S. Appl. No. 10/519,121, filed Dec. 23, 2004, 8 pages.

U.S. Office Action mailed on Jan. 31, 2007, for U.S. Appl. No. 11/078,083, filed Mar. 11, 2005, 16 pages.

U.S. Office Action mailed on May 17, 2007, for U.S. Appl. No. 10/407,435, filed Apr. 4, 2003, 15 pages.

U.S. Office Action mailed on Aug. 24, 2006, for U.S. Appl. No. 10/407,435, filed Apr. 4, 2003, 9 pages.

U.S. Office Action mailed on Jan. 24, 2007, for U.S. Appl. No. 10/701,990, filed Nov. 4, 2003, 6 pages.

U.S. Office Action mailed on Jan. 19, 2007, for U.S. Appl. No. 10/872,280, filed Jun. 17, 2004, 5 pages.

(56) References Cited

OTHER PUBLICATIONS

U.S. Office Action mailed on Jun. 9, 2006, for U.S. Appl. No. 10,872,280, filed Jun. 17, 2004, 6 pages.
U.S. Office Action mailed on Jun. 20, 2005, for U.S. Appl. No. 10,872,280, filed Jun. 17, 2004, 9 pages.
Buchanan, T. A. (2003). "Pancreatic Beta-Cell Loss and Preservation in Type 2 Diabetes," *Clinical Therapeutics* 25(Supplement B):B32-B46.
Edes, T. E. et al. (1998). "Glycemic Index and Insulin Response to a Liquid Nutritional Formula Compared with a Standard Meal," *Journal of the American College of Nutrition* 17(1):30-35.
International Search Report and Written Opinion mailed Aug. 8, 2007, for PCT Application No. PCT/US06/22915 filed Jun. 12, 2006, 8 pages.
Radziuk, J. (2000). "Insulin Sensitivity and its Measurement: Structural Commonalities among the Methods," *The Journal of Endocrinology & Metabolism* 85(12):4426-4433.
"New Diagnostic Technique Could Help Treat AIDS," Agence France-Presse, Dow Jones News/Retrieval, Feb. 17, 1998, pp. 1-2.
Adami, H.O. et al. (1995) "The Aetiology and Pathogenesis of Human Breast Cancer" *Mutation Research* 333: 29-35.
Airhart, J. et al. (1974) "Compartmentation of Free Amino Acids for Protein Synthesis in Rat Liver" *Biochem J.* 140: 539-545.
Ajie, H.O. et al. (1995) "In Vivo Study of the Biosynthesis of Long-Chain Fatty Acids Using Deuterated Water" *Am. J. Physiol.* 269: E247-E252.
Anderson, R.W. et al. (1998) "Direct HIV Cytopathicity Cannot Account for CD4 Decline in AIDS in the Presence of Homeostasis: A Worst-Case Dynamic Analysis" *J. AIDS and Human Retrovirology* 17:245-252.
Antelo, Fernando et al. (2002) "Adipose Triglyceride (TG) Turnover and De Novo Lipogenesis (DNL) in Humans: Measurement by Long-Term 2H2O Labeling and Mass Isotopomer Distribution Analysis (MIDA)" Experimental Biology16 [Meeting Abstract 361.10]: A400.
Asher, E. et al. (1995) "Evaluation of Cell Death in EBV-Transformed Lymphocytes Using Agarose Gel Electrophoresis, Light Microscopy and Electron Microscopy" *Leukemia and Lymphoma* 19:107-119.
Attardi, Giuseppe et al. (1988) "Biogenesis of Mitochondria." *Ann. Rev. Cell. Biol.* 4:289-333.
Bach, Simon P. et al. (2000) "Stem Cells: The Intestinal Stem as a Paradigm" Carcinogenesis 21(3): 469-476.
Bandsma, Robert H.J. et al. (1998) "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile" *Biochem. J.* 329: 699-703.
Bandsma. Robert H.J. et al. (2000) "The Contribution of Newly Synthesized Cholesterol to Bile Salt Synthesis in Rats Quantified By Mass Isotopomer Distribution Analysis" *Biochemica et Biophysica Acta* 1483: 343-351.
Bertani, Roberta et al. (Jan. 2002) "Measurement of Total Body Water (TBW) Through In Vivo Dilution of Tracer Compounds: Use of D2O and its Determination by FT Infrared Spectroscopy" Annali diChimica 92:135-138.
Bickenbach, J.R. (1981) "Identification and Behavior of Label-Retaining Cells in Oral Mucosa and Skin" J Dent Res 1611-1620.
Bier, D.M. (1997) "Stable Isotopes in Biosciences, Their Measurement and Models for Amino Acid Metabolism" *Eur J Pediatr* 156 [Supp. 1]: S2-S8.
Bingham, S.A. (Jan. 1994) "The Use of 24-h Urine Samples and Energy Expenditure to Validate Dietary Assessments" American Journal of Clinical Nutrition 59 [1 Supp.]: 227S-231S.
Black, G.E. et al. (Jan. 2001) "Labeling DNA with Stable Isotopes: Economical and Practical Considerations," *Bio Techniques* 30:134-140.
Blair, Steven N. et al. (1995) "Changes in Physical Fitness and All-Cause Mortality: A Prospective Study of Healthy and Unhealthy Men." JAMA 273(14): 1093-1098.

Blau, K. and Halket, J. eds. (1993) *Handbook of Derivatives for Chromatography*, 2nd Edition, John Wiley &.Sons Ltd., England.
Bonotto, S. et al. (1977) "Study of the Distribution and Biological Effects of 3H in the Algae *Acetabularia, Chlamydomonas* and *Porphyra*" Current Topics in Radiation Quarterly 12: 115-132.
Bravo, Elena et al. (1994) "Decreased Hepatic Uptake and Processing of High Density Lipoprotein Unesterified Cholesterol and Cholesteryl Ester with Age in the Rat" J. Biochem. 116: 1088-1095.
Brown, Alan S. et al (1998) "Treating Patients with Documented Atherosclerosis to National Cholesterol Education Program-Recommended Low-Density-Lipoprotein Cholesterol Goals with Atorvastatin, Fluvastatin, Lovastatin and Simvastatin" J. Am. Coll. Cardiol. 32: 665-672.
Bucy, R.P. et al. (1998) "Analysis of Lymph Node Biopsies in HIV Infected Patients Before and After HAART" Abstract, *5th Conference on Retroviruses and Opportunistic Infections*, Session 66 519:177.
Caldwell, K.A. et al. (1993) "Quantification of Peptide Isotopomer Abundances and Determination of Protein (sic) Turnover Rates by Using Mass Isotopomer Distribution Analysis" Abstract, *41st Annual Amer. Society Mass Spectrometry on Mass Spectrometry*, p. 331a.
Cassella, C.R. et al. (1997) "Mechanisms of Lymphocyte Killing by HIV" Current Opinion in Hematology 4:24-31.
Cesar, D. et al. (1998) "Direct Measurement of CD4+ and CD8+ T Cell Proliferation Rates in Vivo in AIDS Patients Using a Stable Isotope-Mass Spectrometric Technique" Abstract, *5th Conference on Retroviruses and Opportunistic Infections,* Chicago Illinois.
Chinkes, David L. et al. (1996) "Comparison of Mass Isotopomer Dilution Methods Used to Calculate VLDL Production in Vivo" Am. J. Physiol. 271 (Endocrinol. Metab. 34): E373-E383.
Christiansen Mark P. et al. (Oct. 2000) "Effect of Dietary Energy Restriction on Glucose Production and Substrate Utilization in Type 2 Diabetes" Diabetes 49: 1691-1699.
Clayton, David (1991) "Replication and Transcription of Vertebrate Mitochondrial DNA" Annu. Rev. Cell Biol. 7:453-478.
Cohen, A. et al. (1983) "Purine and Pyrimidine Metabolism in Human T Lymphocytes," *J. Biol. Chem.* 258(20):12334-12340.
Cohen, J. (1998) "Failure Isn't What It Used to Be . . . But Neither is Success" *Science* 279:1133-1134.
Collins, M. et al. (Mar. 15, 2000) "A Method for Measuring Mitochondrial Proliferation In Vivo Using 2H20 Incorporation Into Mitochondria DNA," FASEB Journal, 14(4):A620.
Collins, Michelle L. et al. (Jan. 31, 2003) "Measurement of mitochondrial DNA synthesis in vivo using a stable isotope-mass spectrometric technique," J Appl Physiol, 94: 2203-2211.
Conners, M. et al. (1997) "HIV Infection Induces Changes in CD4+ T-Cell Phenotype and Depletions Within the CD4+ T-Cell Repertoire that are not Immediately Restored by Antiviral or Immune-Based Therapies" *Nature Medicine* 3(5):533-540.
Conrads, Thomas P. et al. (Jan. 2002) "Stable Isotope Labeling in Proteomics" The Synthesis Cambridge Isotope Laboratories 3 (2): 1-3.
Craig, Suzanne B. et al. (Sep. 1996) "The Impact of Physical Activity on Lipids, Lipoproteins, and Blood Pressure in Preadolescent Girls" Pediatrics 98 (3): 389-395.
Crain, P.F.(1990) "Preparation and Enzymatic Hydrolysis of DNA and RNA for Mass Spectrometry," *Meth. Enz.* 193:782-790.
Davis, Ajuah et al. (Jul. 2000) "Effect of Pinitol Treatment on Insulin Action in Subjects With Insulin Resistance" Diabetes Care 23 (7):1000-1005.
Deeks, S. et al. (1998) "Viral Load and CD4+ T Cell Changes in Patients Failing Potent Protease Inhibitor Therapy" Abstract, *5th Conference on Retroviruses and Opportunistic Infections,* Session 53, 419:158.
Deeks, Steven G. et al. (2002) "CD4+ T Cell Kinetics and Activation in Human Immunodeficiency Virus-Infected Patients Who Remain Viremic Despite Long-Term Treatment with Protease Inhibitor-Based Therapy" *Journal of Infectious Diseases* 185:315-323.
Dekker, Evelien et al. (1997) "Glucose Homeostasis in Children with Falciparum Malaria: Precursor Supply Limits Gluconeogenesis and Glucose Production" *J Clin Endocrinol Metabol* 82: 2514-2521.
Dimitrov, D.S. et al. (1995) Scientific Correspondence, *Nature* 375:194-195.

(56) References Cited

OTHER PUBLICATIONS

Emken, Edward A. et al. (1983) "Incorporation of deuterium-labeled trans- and cis-13octadeconoic acids in human plasma lipids," Journal of Lipid Research, 24: 34-41.

Etnier, E.L. et al. (1984) "Metabolism of Organically Bound Tritium in Man" Radiat. Res. 100: 487-502.

Fagerquist, Clifton K. et al. (1999) "Molecular Ion Fragmentation and Its Effects on Mass Isotopomer Abundance of Fatty Acid Methyl Estes Ionized By Electron Impact." J Am Soc Mass Spectrom 10: 430-439.

Fagerquist, Clifton K. et al. (2001) "Elimination of the Concentration Dependence in Mass Isotopomer Abundance Mass Spectrometry of Methyl Palmitate Using Metastable Atom Bombardment." J Am Soc Mass Spectrom 12:754-761.

Gorochov, G. et al. (1998) "Perturbation of CD4+ and CD8+ T-Cell Repertoires During Progression to AIDS and Regulation of the CD4+ Repertoire During Antiviral Therapy," Nature Medicine 4(2):215-221.

Goz, Barry (1978) "The Effects of Incorporation of 5-Halogenated Deoxyuridines into DNA of Eukaryotic Cells" Macological Reviews 29, (4): 249-272.

Gratzner, H.G. (1982) "Monoclonal Antibody to 5-Broma-and 5-Iododeoxyuridine: A New Reagent for Detection of DNA Replication" Science 218:474-475.

Guo, Z.K. et al., (2000) "De novo lipogenesis in adipose tissue of lean and obese women: application of deuterated water and isotope ratio mass spectrometry," International Journal of Obesity, 24: 932-937.

Gygi, Steven et al. (2000) "Using Mass Spectrometry for Quantitative Proteomics" Proteomics: A Trends Guide: 31-36.

Hansen, Andrew P. et al. (1992) "A Practical Method for Uniform Isotopic Labeling of Recombinant Proteins in Mammalian Cells" Biochemistry 31 (51): 12713-12718.

Heck, Steven D. et al. (Apr. 1996) "Posttranslational amino acid epimerization: Enzyme-catalyzed isomerization of amino acid residues in peptide chains," Proc. Natl. Acad. Sci. USA, 93(9): 4036-4039.

Hellerstein, M. et al. (1999) "Directly Measured Kinetics of Circulating T Lymphocytes in Normal and HIV-1-Infected Humans" Nature Medicine 5 (1):83-89.

Hellerstein, M. K. et al. (1992) "Mass Isotopomer Distribution Analysis: a Technique for Measuring Biosynthesis and Turnover of Polymers" Am J Physiol 263: E988-E1001.

Hellerstein, M.K. et al. (1994) "Mass Isotopomer Distribution Analysis for Measuring Fluxes Through Intracellular Metabolic Pathways and Biosynthetic Rates of Polymers" IFAC Modeling and Control in Biomedical Systems, pp. 353-359.

Hellerstein, M.K. et al. (1997) "Hepatic Gluconeogenic Fluxes and Glycogen Turnover During Fasting in Humans." J. Clin. Invest. 100(5): 1305-1319.

Hellerstein, M.K. et al. (1997) "T Cell Turnover in HIV-1 Disease," Immunity 7:583-589 (Nov. 1997).

Hellerstein, Marc K. (1995) "Methods for Measurement of Fatty Acid and Cholesterol Metabolism" Current Opinion in Lipidology 6: 172-181.

Hellerstein, Marc K. (1996) "Synthesis of Fat in Response to Alterations in Diet: Insights from New Stable Isotope Methodologies," Lipids, 31(Supp):S117-S125.

Hellerstein, Marc K. (1999) "Measurement of T-Cell Kinetics: Recent Methodologic Advances" Trends Immunology Today 20(10): 438-441.

Hellerstein, Marc K. (1999) "The Changing Face of AIDS: Translators Needed" Am J Clin Nutr 70: 787-788.

Hellerstein, Marc K. (2001) "No Common Energy: de Novo Lipogenesis as the Road Less Traveled" Am J Clin Nutr 74:707-708.

Hellerstein, Marc K. (2002) "Carbohydrate-Induced Hypertriglyceridemia: Modifying Factors and Implications for Cardiovascular Risk" Curr Opin Lipidol 13: 33-40.

Hellerstein, Marc K. (2003) "In Vivo Measurement of Fluxes Through Metabolic Pathways: The Missing Link in Functional Genomics and Pharmaceutical Research" Annu. Rev. Nutr. 23: 379-402.

Hellerstein, Marc K. (2004) "New stable isotope-mass spectrometric techniques for measuring fluxes through intact metabolic pathways in mammalian systems: introduction of moving pictures into functional genomics and biochemical phenotyping," Metabolic Engineering, 6: 85-100.

Hellerstein, Marc K. et al. (1986) "Glycoconjugates as Noninvasive Probes of Intrahepatic Metabolism: Pathways of Glucose Entry into Compartmentalized Hepatic UDP-glucose Pools during Glycogen Accumulation." Proceedings of the National Academy of Sciences of the United States of America 83, Issue 18: 7044-7048.

Hellerstein, Marc K. et al. (1993) "Model for Measuring Absolute Rates of Hepatic de Novo Lipogenesis and Reesterification of Free Fatty Acids." Am. J. Physiol. 265: E814-E820.

Hellerstein, Marc K. et al. (1994) "Effects of Cigarette Smoking and its Cessation on Lipid Metabolism and Energy Expenditure in Heavy Smokers." J. Clin. Invest. 93: 265-272.

Hellerstein, Marc K. et al. (1997) "Altered Fluxes Responsible for Reduced Hepatic Glucose Production and Gluconeogenesis by Exogenous Glucose in Rats." Am. J. Physiol. 272: E163-E172.

Hellerstein, Marc K. et al. (1997) "Measurement of Hepatic Ra UDP-glucose in Vivo in Rats: Relation to Glycogen Deposition and Labeling Patterns" Am. J. Physiol. 272: E155-E162.

Hellerstein, Marc K. et al. (1999) Mass Isotopomer Distribution Analysis at Eight Years: Theoretical, Analytic, and Experimental Considerations. Am. J. Physiol. 276: E1146-E1170.

Hellerstein, Marc K. et al. (2002) "Measurement of Synthesis Rates of Slow-turnover Proteins from 2H2O Incorporation into Non-essential Amino Acids (NEAA) and Application of Mass Isotopomer Distribution Analysis (MIDA)" Faseb Journal Experimental Biology 2002: Meeting Abstracts 16: A256.

Ho, D.D. et al. (1995) "Rapid Turnover of Plasma Virions and CD4 Lymphocytes in HIV-1 Infection," Nature 373:123-126.

Hoh, Rebecca et al. (1998) "De Novo Lipogenesis Predicts Short-Term Body-Composition Response by Bioelectrical Impedance Analysis to Oral Nutritional Supplements in HIV-Associated Wasting." Am. J. Clin. Nutr. 68:154-163.

Hsieh, Elaine A. et al. (2004) "Dynamics of Keratinocytes in Vivo Using 2H2O Labeling: A Sensitive Marker of Epidermal Proliferation State," J Invest Dermatol, 123: 530-536.

Hudgins, Lisa C. et al. (2000) "Relationship Between Carbohydrate-Induced Hypertriglyceridemia and Fatty Synthesis in Lean and Obese Subjects." J. Lipid Res. 41:595-604.

Hudgins, Lisa Cooper et al. (1996) "Human Fatty Acid Synthesis is Stimulated by a Eucaloric Low Fat, High Carbohydrate Diet" J. Clin. Invest. 97(9): 2081-2091.

Humphrey, Thomas J. et al. (1975) "A New Method for the Measurement of Protein Turnover" Biochem. J. 148: 119-127.

Humphrey, Thomas J. et al. (1976) "A Sensitive Method for Measuring Protein Turnover Based on the Measurement of 2-3H-labeled Amino Acids in Proteins" Biochem. J. 156: 561-568.

James, J.S. (1998) "Clinical Implications of Virological Failure: Interview with Steven Deeks, M.D., San Francisco General Hospital," AIDS Treatment News, 289:6-7.

Jennings, Graham et al. (Jul. 1999) "The Use of Infrared Spectrophotometry for Measuring Body Water Spaces." Clinical Chemistry 45(7): 1077-1081.

Jones, Peter J.H. et al. (1994). "Interaction of Dietary Fat Saturation and Cholesterol Level on Cholesterol Synthesis Measured Using Deuterium Incorporation" Journal of Lipid Research 35: 1093-1101.

Jung, Hye Rim. et al. (1999) "Metabolic Adaptations to Dietary Fat Malabsorption in Chylomicron-Deficient Mice" Biochem. J. 343: 473-478.

Jungas, Robert L. (1698) "Fatty Acid Synthesis in Adipose Tissue Incubated in Tritiated Water" Biochemistry 7(10): 3708-3717.

Katz, J. et al. (1976) "Futile Cycles in the Metabolism of Glucose" Curr Top Cell Regul 10: 237-89.

Kelleher, Joanne K. et al. (1992) "Model Equations for Condensation Biosynthesis Using Stable Isotopes and Radioisotopes" Am. J. Physiol. 262: E118-E125.

(56) References Cited

OTHER PUBLICATIONS

Khairallah, Edward A. et al. (1976) "Mortimore. Assessment of Protein Turnover in Perfused Rat Liver: Evidence for Amino Acid Compartmentation from Differential Labeling of Free and tRNA-bound Valine" J Biol Chem 251(5): 1375-1384.
Kim, J. et al. (2000) "A New Stable Isotope-Mass Spectrometric (MS) Method to Measure Proliferation Rates of Colon Epithelial Cells" Faseb Journal 14(4): A718.
Lammert, Ole et al. (2000) "Effects of Isoenergetic Overfeeding of Either Carbohydrate or Fat in Young Men" British Journal of Nutrition 84:233-245.
Lee, Chong Do et al. (1999) "Cardiorespiratory Fitness, Body Composition, and All-Cause and Cardiovascular Disease Mortality in Men 1-3" Am J Clin Nutr 69:373-380.
Leung, Gordon K. et al. (2000) "A Deficiency of Microsomal Triglyceride Transfer Protein Reduces Apolipoprotein B Secretion" The Journal of Biological Chemistry 275(11):7515-7520.
Lewanczuk, Richard Z. et al. (2004) "Comparison of the [13 C] Glucose Breath Test to the Hyperinsulinemic-Euglycemic Clamp When Determining Insulin Resistance" Diabetes Care 27(2):441-447.
Lipkin, M. (1987) "Proliferation and Differentiation of Normal and Diseased Gastrointestinal Cells" In *Physiology of the Gastrointestinal Tract*, L.R. Johnson ed., Raven Press, New York, pp. 255-284.
Lipkin, Martin et al. (1963) "Cell Proliferation Kinetics in the Gastrointestinal Tract of Man. I. Cell Renewal in Colon and Rectum" Journal of Clinical Investigations 42(6):767-776.
Lutton, C. et al. (1990) "Critical analysis of the Use of 14C-acetate for Measuring In Vivo Rat Cholesterol Synthesis," Reprod Nutr Dev, 30: 71-84.
MacAllan, Derek C. et al. (1998) "Measurement of Cell Proliferation by Labeling of DNA with Stable Isotope-Labeled Glucose: Studies in Vitro, in Animals, and in Humans" Proc. Natl. Acad. Sci. 95: 708-713.
Maentausta, O. et al. (1979) "Radioimmunoassay of Conjugated Cholic Acid, Chenodeoxycholic Acid, and Deoxycholic Acid from Human Serum, with Use of 125I-Labeled Ligands" Clin. Chem. 25(2): 264-268.
Margolick, J.B. et al. (1995) "Failure of T-cell Homeostasis Preceding AIDS in HIV-1 Infection," Nature Medicine, 1(7):674-680.
Mathur-De Vré, R. et al. (1984) "Molecular Aspects of Tritiated Water and Natural Water in Radiation Biology" Prog. Biophys. Molec. Biol. 43: 161-193.
McCloskey, J.A. (1990) "ElectronIonization Mass Spectra of Trimethylsilyl Derivatives of Nucleosides," *Meth. Enz.* 193:825-841.
McCune, J.M. (1997) "Thymic Function in HIV-1 Disease," *Seminars in Immunology* 9:397-404.
McCune, Joseph M. et al. (2000) "Factors Influencing T-Cell Turnover in HIV-1-Seropositive Patients" J. Clin. Invest. 105:R1-R8.
McLean, A.R. et al. (1995) "In Vivo Estimates of Division and Death Rates of Human T Lymphocytes," *Proc. Natl. Acad. Sci USA* 92:3707-3711.
Meier, P.R. et al. (Mar. 1981) "Rates of Protein Synthesis and Turnover in Fetal Life," Am J Physiol., 240(3):E320-E324.
Mellors, J.W. et al. (1995) "Quantitation of HIV-1 RNA in Plasma Predicts Outcome after Seroconversion," *Ann. Intern. Med.* 122:573-579.
Mellors, J.W. et al. (1996) "Prognosis in HIV-1 Infection Predicted by the Quantity of Virus in Plasma," *Science*, 272:1167-70.
Messmer, Bradley T. et al. (Feb. 10, 2005) "In Vivo Measurements Document the Dynamic Cellular Kinetics of Chronic Lymphocytic Leukemia B Cells," J. Clin. Invest. doi:10.1172/JCI200523409.
Mewissen, D.J. et al. (1977) "Comparative Incorporation of Tritium from Tritiated Water Versus Tritiated Thymidine, Uridine or Leucine" Curr Top Rad Res Quart 12: 225-254.
Michie, C.A. et al. (1992) "Lifespan of Human Lymphocyte Subsets Defined by CD45 Isoforms," Nature 360:264-265.

Misell, L. et al. (2000) "A new in Vivo Stable Isotope Method for Measuring Mammary Epithelial Cell Proliferation" Faseb Journal Experimental Biology 2000 14(4), Meeting Abstract 550.5: A786.
Mohri, Hiroshi et al. (2001) "Increased Turnover of T Lymphocytes in HIV-1 Infection and its Reduction by Antiretroviral Therapy." J. Exp. Med. 194(9): 1277-1287.
Morris, Rebecca J. et al. (1997) "Evidence that a Slowly Cyling Subpopulation of Adult Murine Epidermal Cells Retains Carcinogen" Cancer Research 46: 3061-3066.
Morris, Rebecca J. et al. (1997) "Evidence that Cutaneous Carcinogen-initiated Epithelial Cells from Mice are Quiescent Rather than Actively Cyling" Cancer Research 57:3436-3443.
Morsches, Bernhard (1976) "Tierexperimentelle Untersuchungen uber die Beziehungen zwischen der Hydroxyprolinausscheidung im Urin und den Hydroxyprolinfraktionen im Serum," Der Hautarzt, 27: 234-242.
Mosier, D.E. (1995) "CD4.sup.+ Cell Turnover," *Nature* 375:193-194.
Murali-Krishna, K. et al. (1998) "Counting Antigen-Specific CD8 T Cells: A Reevaluation of Bystander Activation during Viral Infection," *Immunity* 8:177-187.
Nagasaka, Shoichiro et al. (May 1999) "Endogenous Glucose Production and Glucose Effectiveness in Type 2 Diabetic Subjects Derived From Stable-Labeled Minimal Modal Approach," Diabetes, 48: 1054-1056.
Neese, R. A. et al. (1993) "Measurement of Endogenous Synthesis of Plasma Cholesterol in Rats and Humans Using MIDA" Am. J. Physiol. 264: E139-E147.
Neese, R. A. et al. (Nov. 2002) "Measurement in Vivo of Proliferation Rates of Slow Turnover Cells by 2H2O Labeling of the Deoxyribose Moiety of DNA," PNAS, 99(24): 15345-15350.
Neese, Richard A. et al. (1995) "Gluconeogenesis and Intrahepatic Triose Phosphate Flux in Response to Fasting or Substrate Loads" Journal of Biological Chemistry 270(24): 14452-14463.
Neese, Richard A. et al. (2001) "Advances in the Stable Isotope-Mass Spectrometric Measurement of DNA Synthesis and Cell Proliferation" Analytical Biochemistry 298(2): 189-195.
Ong, Shao-En et al. (2002) "Stable Isotope Labeling by Amino Acids in Cell Culture, SILAC, as a Simple and Accurate Approach to Expression Proteomics" *Molecular and Cellular Proteomics* 1: 376-386.
Ouguerram, K. et al. (Jan. 2002) "A New Labeling Approach Using Stable Isotopes to Study In Vivo Plasma Cholesterol Metabolism in Humans," Metabolism, 51(1): 5-11.
Oyaizu, N. et al. (1995) "Role of Apoptosis in HIV Disease Pathogenesis," *J. of Clinical Immunology* 15(5):217-231.
Palmer, L.D. et al. (1997) "Telomere Length, Telomerase Activity, and Replicative Potential in HIV Infection: Analysis of CD4+ and CD8+ T Cells from HIV-discordant Monozygotic Twins," *J. Experimental Medicine* 185(7):1381-1386.
Panteleo, Giuseppe (1999) "Unraveling the Strands of HIV's Web" Nature Medicine 5(1): 27-28.
Papageorgopoulos, C. et al.(1993) "Toward the Measurement of Protein Synthesis by Mass Isotopomer Distribution Analysis (MIDA):Resolution of Isotopomers in a [d.sub.3 ]-Leucine Enriched Synthetic Oligopeptide Using Electrospray/Quadrupole Mass Spectrometry (ESI/MS)," Abstract, *Federation of American Societies for Experimental Biology* 1022:A177.
Papageorgopoulos, Christina et al. (1999) "Measuring Protein Synthesis by Mass Isotopomer Distribution Analysis (MIDA)" Analytical Biochemistry 267: 1-16.
Park, S. S., et al. (1997) "Measurement of Small Intestinal Cell Turnover with [6,6, 2H2] Glucose," *Berkeley Scientific*, Abstract 1(2):41-43.
Parks, Elizabeth J. et al. (1999) "Effects of a Low-Fat, High-Carbohydrate Diet on VLDL-Triglyceride Assembly, Production, and Clearance" J. Clin. Invest. 104(8): 1087-1096.
Parks, Elizabeth J. et al. (2000) "Carbohydrate-induced Hypertriacylglycerolemia: Historical Perspective and Review of Biological Mechanisms" Am. J. Nutr. 71: 412-433.
Parks, Elizabeth J. et al. (2000) "Dependence of Plasma a-Tocopherol Flux on Very Low-Density Triglyceride Clearance in Humans" Free Radical Biology & Medicine 29(11): 1151-1159.

(56) References Cited

OTHER PUBLICATIONS

Paša-Tolic, Ljiljana et al. (1999) "High Throughput Proteome-Wide Precision Measurements of Protein expression Using Mass Spectrometry" *J. Am. Chem. Soc.* 121: 7949-7950.

Patterson, Bruce W. et al. (1993) "Concentration Dependence of Methyl-Palmitate Isotope Ratios by Electron Impact Ionization Gas Chromatography/Mass Spectrometry" Biol. Mass Spectrom. 22: 481-486.

Patterson, Bruce W. et al. (Aug. 1997) "Measurement of Very Low Stable Isotope Enrichments by Gas Chromatography/Mass Spectrometry: Application to Measurement of Muscle Protein Synthesis," Metabolism, 46(8): 943-948.

Patton, G.M. et al. (Jul. 1979) "Measurements of Fatty Acid Synthesis by Incorporation of Deuterium from Deuterated Water," Biochemistry, 18(14):3186-3188.

Perelson, A.S. et al.(1996) "HIV-1 Dynamics in Vivo: Virion Clearance Rate, Infected Cell Life-Span, and Viral Generation Time," *Science* 271:1582-1586.

Perelson, A.S. et al.(1997) "Decay Characteristics of HIV-1-Infected Compartments During Combination Therapy," *Nature* 387:188-191.

Pozharisski, K.M. et al. (1980) "Study of Kinetics of Epithelial Cell Populations in Normal Tissues of the Rat's Intestines and in Carcinogenesis." Exp. Path., Bd. 18:387-406.

Previs, Stephen F. et al. (2001) "Estimation of Protein Turnover In Vivo Using D2O" Diabetes Abstract Book, 61st Scientific Sessions 50[Supplement 2]: A301.

Ravichandran, L.V. et al., (Jun. 1991) "In vivo labeling studies on the biosynthesis and degradation of collagen in experimental myocardial infarction," Biochemistry Journal, 24(3): 405-414.

Reichard, P. (1978) "From Deoxynucleotides to DNA Synthesis," *Federation Proceedings* 37(1):9-14.

Reichard, P. (1988) "Interactions Between Deoxyribonucleotide and DNA Synthesis," *Ann. Rev. Biochem.* 57:349-374.

Roberts, S.B. (1989) "Use of the Doubly Labeled Water Method for Measurement of Energy Expenditure, Total Body Water, Water Intake, and Metabolizable Energy Intake in Humans and Small Animals" Can. J. Physiol. Pharmacol. 67(10): 1190-1198.

Robin, Eugene D. et al. (1988) "Mitochondria DNA Molecules and Virtual Number of Mitochondria per Cell in Mammalian Cells" *Journal of Cellular Physiology* 136:507-513.

Rocha, B. et al. (1990) "Accumulation of Bromodeoxyuridine-Labelled Cells in Central and Peripheral Lymphoid Organs: Minimal Estimates of Production and Turnover Rates of Mature Lymphocytes" *Eur. J. Immunol.* 20:1697-1708.

Roda, Aldo et al. (1980) "Results with Six 'Kit' Radioimmunoassays for Primary Bile Acids in Human Serum Intercompared" Clin. Chem. 26(12): 1677-1682.

Roederer, M. (Jul. 1995) "T-Dell Dynamics of Immunodeficiency," *Nature Medicine* 1(7):621-622.

Rooyackers, Olav E. et al. (Oct. 1996) "Tracer Kinetics Are of Limited Value to Measure In Vivo Protein Synthesis and Degradation Rates in Muscle of Anesthetized Rats," Metabolism, 45(10): 1279-1283.

Sawada, S. et al. (1995) "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998) "Tracking T-Cells in AIDS Patients: A Safe Reliable Method of Measuring Human Cell Generation Rates," *Berkeleyan*, p. 3.

Scheibner, Jurgen et al. (1993) "Bile Acid Synthesis from Newly Synthesized Vs. Preformed Cholesterol Precursor Pools in the Rat," Hepatology, 17: 1095-1102.

Scheibner, Jurgen et al. (1999) "Complex Feedback Regulation of Bile Acid Synthesis in the Hamster: The Role of Newly Synthesized Cholesterol," Hepatology, 30: 230-237.

Schwarz, Jean-Marc et al. (1995) "Short-Term Alterations in Carbohydrate Energy Intake in Humans" J. Clin. Invest. 96: 2735-2743.

Shevchenko, Andrej et al. (1997) "Rapid 'de Novo' Peptide Sequencing by a Combination of Nanoelectrospray, Isotopic Labeling and a Quadrupole/Time-of-flight Mass Spectrometer" Rapid Commun. Mass Spectrom. 11: 1015-1024.

Shigenaga, M.K. et al. (1994) "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection," *Methods in Enzymology* 234:16-33.

Siler, Scott Q. et al. (1998) "The Inhibition of Gluconeogenesis Following Alcohol in Humans" Am. J. Physiol. 275: E897-E907.

Siler, Scott Q. et al. (1998) "VLDL-Triglyceride Production After Alcohol Ingestion, Studied Using [2-13C1] Glycerol" J. Lipid Res. 39: 2319-2328.

Smith, et al. (1983) "The Phosphogluconate Odixative Pathway," in *Principles of Biochemistry*, 7th edition, McGraw-Hill Book Company, pp. 417-423.

Sprent, J. et al. (1995) "CD4+ Cell Turnover," *Nature* 375:194.

Sunter, J.P. et al. (1978) "Cell Population Kinetics in the Epithelium of the Colon of the Male Rat." Virchows Archiv. B Cell Path. 26: 275-287.

Teixeira, Luciléia et al. (2001) "Poor CD4 T Cell Restoration After Supression of HIV-1 Replication May Reflect Lower Thymic Function" AIDS 15(14):1749-1756.

Tint, G.S. et al. (1974) "Transformation of 5α-cholest-7-en-3β-ol to Cholesterol and Cholestanol in Cerebrotendinous Xanthomatosis" Journal of Lipid Research 15: 256-262.

Traber, P.G. et al. (1991) "Isolation of Intestinal Epithelial Cells for the Study of Differential Gene Expression Along the Crypt-Villus Axis," *Am. J. Physiol.* 260:G895-G903.

Trappe, T. A. et al. (2002) "Effect of Ibuprofen and Acetaminophen on Postexercise Muscle Protein Synthesis" Am J Physiol Endocronol Metab 282: E551-E556.

Turner, Scott M. et al. (2002) "Measurement of Triglyceride (TG) Synthesis in Vivo 2H2O Incorporation into TG-Glycerol and Application of Mass Isotopomer Distribution Analysis (MIDA)." Experimental Biology 2002 16[Meeting Abstract 361.9]: A400.

Van Hinsbergh, V.W.M. et al. (1978) "Palmitate Oxidation by Rat Skeletal Muscle Mitochondria" Archives of Biochemistry and Biophysics 190(2): 762-771.

Van Loan, Marta D. et al. (1999) "Monitoring Changes in Fat-Free Mass in HIV-Positive Men With Hypotestosteronemia and AIDS Wasting Syndrome Treated With Gonadal Hormone Replacement Therapy" AIDS 13:241-248.

Veenstra, Timothy D. et al. (2000) "Proteome Analysis Using Selective Incorporation of Isotopically Labeled Amino Acids" *J. Am. Soc. Mass. Spectrom.* 11: 78-82.

Veerkamp, Jacques H. et al. (1986) "14CO2 Production Is No Adequate Measure of [14C]Fatty Acid Oxidation" Biochemical Medicine and Metabolic Biology 35: 248-259.

Véniant, Murielle M. et al. (2000) "Defining the Atherogenicity of Large and Small Lipoproteins Containing Apolipoproteins B100" J. Clin. Invest. 106(12): 1501-1510.

Wadke, M. et al. (Jul. 1973) "Fatty Acid Synthesis by Liver Perfused with Deuterated and Tritiated Water," Biochemistry., 12(14):2619-2624.

Wain-Hobson, S. (1995) "Virological Mayhem," *Nature* 373:102.

Waldeman, F.M. et al. (1991) "A Comparison Between Bromodeoxyuridine and 3 H Thymidine Labeling in Human Breast Tumors," *Modern Path.* 4(6):718-722.

Wang, Wei et al. (2000) "Effects of Nicotinic Acid on Fatty Acid Kinetics, Fuel Selection, and Pathways of Glucose Production in Women." Am. J. Physiol. Endocrinol. Metab. 279: E50-E59.

Waterlow, J.C. (1980) "Protein Turnover in the Whole Animal" Invest. Cell Pathol. 3: 107-119.

Wei, X et al. (1995) "Viral Dynamics in Human Immunodeficiency Virus Type 1 Infection," *Nature* 373:117-122.

Winett, Richard et al. (2000) "Exercise Regimens for Men With HIV." JAMA 284(2): 175-6.

Wolf, George (1995) "The Effect of Fasting and Fructose and Glucose Infusion on Gluconeogenesis and Triose Phosphate Flux in Rats in Vivo" Nutrition Reviews 53(10): 299-302.

(56) References Cited

OTHER PUBLICATIONS

Wolfe, R. (1990) "Isotopic Measurement of Glucose and Lactate Kinetics," *Ann. Med.* 22:163-170.
Wolthers et al. (1998) "Rapid CD4+ T-Cell Turnover in HIV-1 Infection: a Paradigm Revisited," *Immunol. Today* 19(1):44-48.
Wolthers, K.C. et al. (1996) "T Cell Telomere Length in HIV-1 Infection: No Evidence for Increased CD4+ T Cell Turnover," *Science* 274:1543-1547.
Wood, H.G. et al. (1963) "Estimation of Pathways of Carbohydrate Metabolism," *Biochemische Zeitschrift* 338:809-847.
Zhang, Z-Q. et al. (Feb. 1998) "Kinetics of CD4+ T Cell Repopulation of Lymphoid Tissues after Treatment of HIV-1 Infection," *Proc. Natl. Acad. Sci. USA* 95:1154-1159.
Zilversmit, D.B. et al. (1943) "On the Calculation of 'Turnover Time' and 'Turnover Rate' from Experiments Involving the Use of Labeling Agents," *J. of General Physiology* 26(3):325-331.
Lefebvre, P. J. (Jan. 1979). "Naturally Labeled 13C-Glucose: A New Tool to Measure Oxidation Rates of Exogenous Glucose," *Diabetes* 28(Suppl. 1): 63-65.
Royale, G. T. et al. (1981). "Techniques for Investigating Substrate Metabolism in Patients," *Annals of the Royal College of Surgeons of England* 63:415-419.
Bier, D. M. (Nov. 1987). "The Use of Stable Isotopes in Metabolic Investigation," *Balliere's Clinical Endocrinology and Metabolism* 1(4):817-836.
Schneiter, P. et al. (1998). "Kinetics of Dexamethasone Induced Alterations of Glucose Metabolism in Healthy Humans," *American Journal of Physiology*, pp. E806-E813.
Supplementary Partial European Search Report mailed Sep. 22, 2006, for European patent application No. EP 03768624.3, filed Nov. 4, 2003, 4 pages.
Di Buono, M. et al. (2000). "Comparison of Deuterium Incorporation and Mass Isotopomer Distribution Analysis for Measurement of Human Cholesterol Biosynthesis," *Journal of Lipid Research* 41:1516-1523.
Rittenberg, D. et al. (Feb. 1937). "Deuterium as an Indicator in the Study of Intermediary Metabolism—VIII. Hydrogenation of Fatty Acids in the Animal Organism," *Journal of Biological Chemistry* 117:485-490.
Rittenberg, D. et al. (Sep. 1937). "Deuterium as an Indicator in the Study of Intermediary Metabolism—X. The Metabolism of Butyric and Caproic Acids," *Journal of Biological Chemistry* 120:503-510.
Schoenheimer, R. et al. (Mar. 1936). "Deuterium as an Indicator in the Study of Intermediary Metabolism—V. The Desaturation of Fatty Acids in Organism," *Journal of Biological Chemistry* 113:505-510.
Gasparini, P. et al. (Mar. 1989). "Amplification of DNA from Epithelial Cells in Urine," *The New England Journal of Medicine* 320(12):809.
Patsalos, P. N. et al. (Oct. 1980). "Pattern of Myelin Breakdown During Sciatic Nerve Wallerian Degeneration: Reversal of the Order of Assembly," *The Journal of Cell Biology* 87:1-5.
Wolfe, R. et al. (1984). "Glucose Metabolism in Humans," ACS Symposium Series 258, Chapter 12, Turnund et al. ed., pp. 175-189.
Jones, P. J. J. et al. (1990). "Evidence for Diurnal Periodicity in Human Cholesterol Synthesis," *Journal of Lipid Research* 31:667-673.
Iyengar, V. et al. (1991). "Human Stools as a Source of Viable Colonic Epithelial Cells," *The FASEB Journal* 5:2856-2859.
Emken, E. A. (1994). "Metabolism of Dietary Stearic Acid Relative to Other Fatty Acids in Human Subjects," *The American Journal of Clinical Nutrition* 60(Suppl):1023S-1028S.
Mindham, M. A. et al. (1994). "Application of Simultaneous Spleen and Liver Perfusion to the Study of Reverse Cholesterol Transport," *Biochemical Journal* 302:207:213.
Gerling, B. et al. (1997). "Prediction of Liver Fibrosis According to Serum Collagen VI Level in Children with Cystic Fibrosis," The New England Journal of Medicine 336(22):1611-1612.
Perochon, E. et al. (1997). "Radiolabeling of the Lipids of Chinese Hamster Ovary Cells with the Probe [3-(Trifluoromethyl)-3-(m-[$^{125}$I]iodophenyl)diazirine]," *Analytical Biochemistry* 254:109-118.

Rosin, M. P. et al. (Dec. 1, 1997). "The Use of Exfoliative Cell Samples to Map Clonal Genetic Alterations in the Oral Epithelium of High-Risk Patients," *Cancer Research* 57:5258-5260.
Dalvie, D. (2000). "Recent Advances in the Applications of Radioisotopes in Drug Metabolism, Toxicology and Pharmacokinetics," *Current Pharmaceutical Design* 6:1009-1028.
Sosa-Peinado, A. et al. (Jul. 2000). "Overexpression and Biosynthetic Deuterium Enrichment of TEM-1 Beta-Lactamase for Structural Characterization by Magnetic Resonance Methods," *Protein Expression and Purification* 19(2):235-245.
Ackermans, M. T. et al. (2001). "The Quantification of Gluconeogenesis in Healthy Men by $^2H_2O$ and $[2-^{13}C]$Glycerol Yields Different Results: Rates of Gluconeogenesis in Healthy Men Measured with $^2H_2O$ are Higher than those Measured with $[2-^{13}C]$Glycerol," *The Journal of Clinical Endocrinology & Metabolism* 86(5):2220-2226.
Hulzebos, C. V. et al. (2001). "Measurement of Parameters of Cholic Acid Kinetics in Plasma using a Microscale Stable Isotope Dilution Technique: Application to Rodents and Humans" *Journal of Lipid Research* 42:1923-1929.
Nanjee, M. N. et al. (2001). "Intravenous apoA-I/lecithin Discs Increase Pre-Beta-HDL Concentration in Tissue Fluid and Stimulate Reverse Cholesterol Transport in Humans," *Journal of Lipid Research* 42:1586-1593.
Paku, S. (Apr. 2001). "Origin and Structural Evolution of the Early Proliferating Oval Cells in Rat Liver," *American Journal of Pathology* 158(4):1313-1323.
Sting et al. (2001). Breast Can Res and Treatment, 67:93-109.
Oshima, M. et al. (2002). "COX Selectivity and Animal Models for Colon Cancer," *Current Pharmaceutical Design* 8:1021-1034.
Robosky, L. C. (2002). "In Vivo Toxicity Screening Programs Using Metabonomics," *Combinatorial Chemistry & High Throughput Screening* 5:651-662.
Mikkola, T. S. et al. (2003). "Serum Cholesterol Efflux Potential is an Independent Predictor of Coronary Artery Atherosclerosis," *Atherosclerosis* 170:31-38.
Propper, D. J. et al. (Jan. 2003). "Use of Positron Emission Tomography in Pharmacokinetic Studies to Investigate Therapeutic Advantage in a Phase I Study of 120-Hour Intravenous Infusion XR5000," Journal of Clinical Oncology 21(2):203-210.
Rittler, P. et al. (2003). "Effect of Tumor Removal on Mucosal Protein Synthesis in Patients with Colorectal Cancer," *American Journal of Physiology-Endocrinology and Metabolism* 284:E1018-E1021.
International Search Report mailed on Apr. 13, 2004, for PCT application No. PCT/US03/20052 filed on Jun. 25, 2003, 3 pages.
International Search Report mailed on Jun. 29, 2004, for PCT application No. PCT/US03/04183 filed on Feb. 12, 2003, 4 pages.
International Search Report mailed Jul. 8, 2004, for PCT patent application No. PCT/US03/27623 filed on Sep. 4, 2003, 4 pages.
International Search Report mailed on Jul. 9, 2004, for PCT application No. PCT/US03/35107 filed on Nov. 4, 2003, 2 pages.
International Search Report mailed Aug. 18, 2004, for PCT application PCT/US03/23340, filed Jul. 25, 2003, 2004: 4 pages.
International Search Report mailed on Aug. 18, 2004, for PCT application PCT/US03/29526, filed Sep. 16, 2003, 3 pages.
International Search Report mailed on Aug. 20, 2004, for PCT application No. PCT/US03/10554 filed on Apr. 4, 2003, 4 pages.
Marin, S. et al. (2004). "Dynamic Profiling of the Glucose Metabolic Network in Fasted Rat Hepatocytes using $[1,2-^{13}C_2]$Glucose," *Biochemical Journal* 381:287-294.
Australian Patent Office Search Report mailed Aug. 26, 2005, for Singapore patent application No. SG 200500571-5, filed Jul. 25, 2003, 5 pages.
Clarke, R. B. (2005). "Isolation and Characterization of Human Mammary Stem Cells," *Cell Proliferation* 38:375-386.
International Search Report mailed on Jan. 19, 2005, for PCT application No. PCT/US03/29361 filed on Sep. 15, 2003, 4 pages.
International Search Report mailed on Mar. 25, 2005, for PCT application No. PCT/US04/39722 filed on Nov. 24, 2004, 3 pages.
International Search Report mailed on Apr. 4, 2005, for PCT application No. PCT//US04/21063 filed on Jun. 29, 2004, 2 pages.
International Search Report mailed Aug. 1, 2005, for PCT application No. PCT/US2005/08265, filed Mar. 11, 2005, 4 pages.

(56) References Cited

OTHER PUBLICATIONS

Supplementary Partial European Search Report mailed Aug. 17, 2005, for EP Application No. 03749756.7 filed Sep. 15, 2003, 6 pages.
International Search Report and Written Opinion mailed Aug. 8, 2006, for international application No. PCT/US05/10429, filed Mar. 29, 2005, 15 pages.
Naik, S. U. et al. (2006). "Pharmacological Activation of Liver X Receptors Promotes Reverse Cholesterol Transport In Vivo," *Circulation* 113:90-97.
Sting et al. (Feb. 2006). *Nature* 439:993-997.
Supplementary Partial European Search Report mailed Mar. 9, 2006, for European Patent Application No. EP 03713429.3, filed Feb. 12, 2003, 6 pages.
Supplementary Partial European Search Report mailed Jul. 25, 2006, for EP Application No. 02806603.3 filed Oct. 23, 2002, 5 pages.
Written Opinion mailed Jul. 14, 2006, by the Australian Patent Office for Singapore patent application No. 200502593-7, filed Nov. 4, 2003, 5 pages.
International Search Report and Written Opinion mailed Feb. 5, 2008, for PCT Application No. PCT/US2006/017167 filed May 3, 2006, 11 pages.
"NCBI Blast: Protein Sequence (17 letters)," located at <http://blast.ncbi.nlm.nih.gov/Blast.cgi> visited on May 29, 2008, 5 pages.
Austrian Search Report and Written Opinion mailed Aug. 5, 2009, for SG Application No. 200717391-7 filed May 3, 2006, 7 pages.
Supplementary European Search Report mailed Jun. 30, 2009, for EP Application No. 05725448.4 filed Mar. 11, 2005, 7 pages.
Supplementary European Search Report mailed Jul. 28, 2009, for EP Application No. 04809469.2 filed Jun. 29, 2004, 4 pages.
Landau et al., "Use of 2H2O for Estimating Rates of Gluconeogenesis", Journal of Clinical Investigation, vol. 95, Jan. 1995, pp. 172-178.
Bantscheff et al., "Quantitative mass spectrometry in proteomics: a critical review", Analytical and Bioanalytical Chemistry, vol. 389, 2007, pp. 1017-1031.
Extended European Search Report received for European Patent Application No. 06759050.5, mailed on Mar. 31, 2011, 7 pages.
Wang et al., "Validation of a Single-Isotope-Labeled Cholesterol Tracer Approach for Measuring Human Cholesterol Absorption", Lipids, vol. 39, No. 1, 2004, pp. 87-91.
Jones et al., "Modulation of plasma lipid levels and cholesterol kinetics by phytosterol versus phytostanol esters", Journal of Lipid Research, vol. 41, 2000, pp. 697-705.
Extended European Search Report received for European Patent Application No. 06784805.1, mailed on Mar. 21, 2011, 7 pages.
Shen et al., "Purification of oligodendrocyte and its myelination to the demyelinated culture model in vitro", Acta Histochem. Cytochem., vol. 35, No. 2, 2002, p. 123.
Murphy et al., "A new Sensitive In Vivo Diagnostic Test of Insulin Resistance: The Deuterated Oral Glucose Tolerance Test (2H-OGTT)", Diabetes, American Diabetes Association, vol. 53, No. Suppl. 02, Jan. 1, 2004, 2 pages.
Office Action received for European Patent Application No. 06759050.5, mailed on Apr. 19, 2011, 1 page.
Office Action received for European Patent Application No. 06784805.1, mailed on Apr. 7, 2011, 1 page.
McFarland et al., "Inhibition of DNA synthesis in neonatal rat brain regions caused by acute nicotine administration", Developmental Brain Research, vol. 58, No. 2, Feb. 22, 1991, pp. 223-229.
Ramakers et al., "Chronic suppression of bioelectric activity and cell survival in primary cultures of rat cerebral cortex: biochemical observations", European Journal of Neuroscience, vol. 3, No. 2, Feb. 1991, pp. 154-161.
European Search Report received for EP Patent Application No. 04812281.6, mailed on Oct. 6, 2010, 4 pages.
Hellerstein et al., "Subpopulations of long-lived and short-lived T cells in advanced HIV-1 infection", The Journal of Clinical Investigation, vol. 112, No. 6, Sep. 2003, pp. 956-966.
Siler et al., "De novo lipogenesis, lipid kinetics, and whole-body lipid balances in humans after acute alcohol consumption1-3", The American Journal of Clinical Nutrition, vol. 70, 1999, pp. 928-936.
Office Action received for European Patent Application No. 06759050.5, mailed on Nov. 21, 2011, 6 pages.
Notice of Allowance received for U.S. Appl. No. 12/534,807 mailed on Nov. 15, 2011, 10 pages.
Ferezou et al., "Origins of Neutral Sterols in Human Feces Studied by Stable Isotope Labeling (D and 13C). Existence of an External Secretion of Cholesterol", Digestion, vol. 21, 1981, pp. 232-243.
Office Action received for European Patent Application No. 06784805.1, mailed on Dec. 23, 2011, 5 pages.
Chobanian et al., "Body Cholesterol Metabolism in Man. II. Measurement of the Body Cholesterol Miscible Pool and Turnover Rate", Journal of Clinical Investigation, vol. 41, No. 9, 1962, pp. 1738-1744.
Duane, William C., "Measurement of Bile Acid Synthesis by Three Different Methods in Hypertriglyceridemic and Control Subjects", Journal of Lipid Research, vol. 38, 1997, pp. 183-188.
Martin et al. (1998). "Discovery of a human liver glycogen phosphorylase inhibitor that lowers blood glucose in vivo," *Proc. Natl. Acad. Sci. USA* 95(4):1776-1781.
Backhouse, B. et al. (Mar. 1982). "Effects of haloperidol on cell proliferation in the early postnatal rat brain," *Neuropathology and Applied Neurobiology* 8(2):109-116.
Malberg, J. et al. (Dec. 15, 2000). "Chronic antidepressant treatment increases neurogenesis in adult rat hippocampus," *J Neuroscience* 20(24):9104-9110.
Santarelli, L. et al. (Oct. 8, 2003). "Requirement of hippocampal neurogenesis for the behavioral effects of antidepressants," *Science* 301:805-809.
Wong, M-L et al. (Jan. 30, 2004). "From monoamines to genomic targets: a paradigm shift for drug discovery in depression," *Nature Reviews: Drug Discovery* 3(2):136-151.
Tayek et al., "Glucose production, recycling, and gluconeogenesis in normals and diabetics: a mass isotopomer [U-13C]glucose study", The American Journal of Physiology, vol. 270, 1996, pp. E709-E717.
Whittmann and Heinzle (2001). "Application of MALDI-TOF MS to lysine-producing *Corynebacterium glutamicum*: a novel approach for metabolic flux analysis," *Eur. J. Biochem.* 268:2441-2455.
Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.
Price et al., "Measurement of Human Plasma Proteome Dynamics with 2H2O and Liquid Chromatography Tandem Mass Spectrometry", Analytical Biochemistry, vol. 420, 2012, pp. 73-83.
Hinkson et al., "The Dynamic State of Protein Turnover: It's About Time", Trends in Cell Biology, vol. 21, No. 5, May 2011, pp. 293-303.
Office Action received for European Patent Application No. 06784805.1, mailed on Dec. 10, 2012, 3 pages.
Nordhoff et al., "Mass Spectrometry of Nucleic Acids", Mass Spectrometry Reviews, vol. 15, 1996, pp. 67-138.
Previs et al., "A Critical Evaluation of Mass Isotopomer Distribution Analysis of Gluconeogenesis in Vivo", American Journal of Physiology-Endocrinology and Metabolism, vol. 277, 1999, E154-E160.
Szymanski et al., "Beyond the Proteome: Non-Coding Regulatory RNAs", Genome Biology, vol. 3, No. 5, Apr. 15, 2002, pp. 1-8.

\* cited by examiner

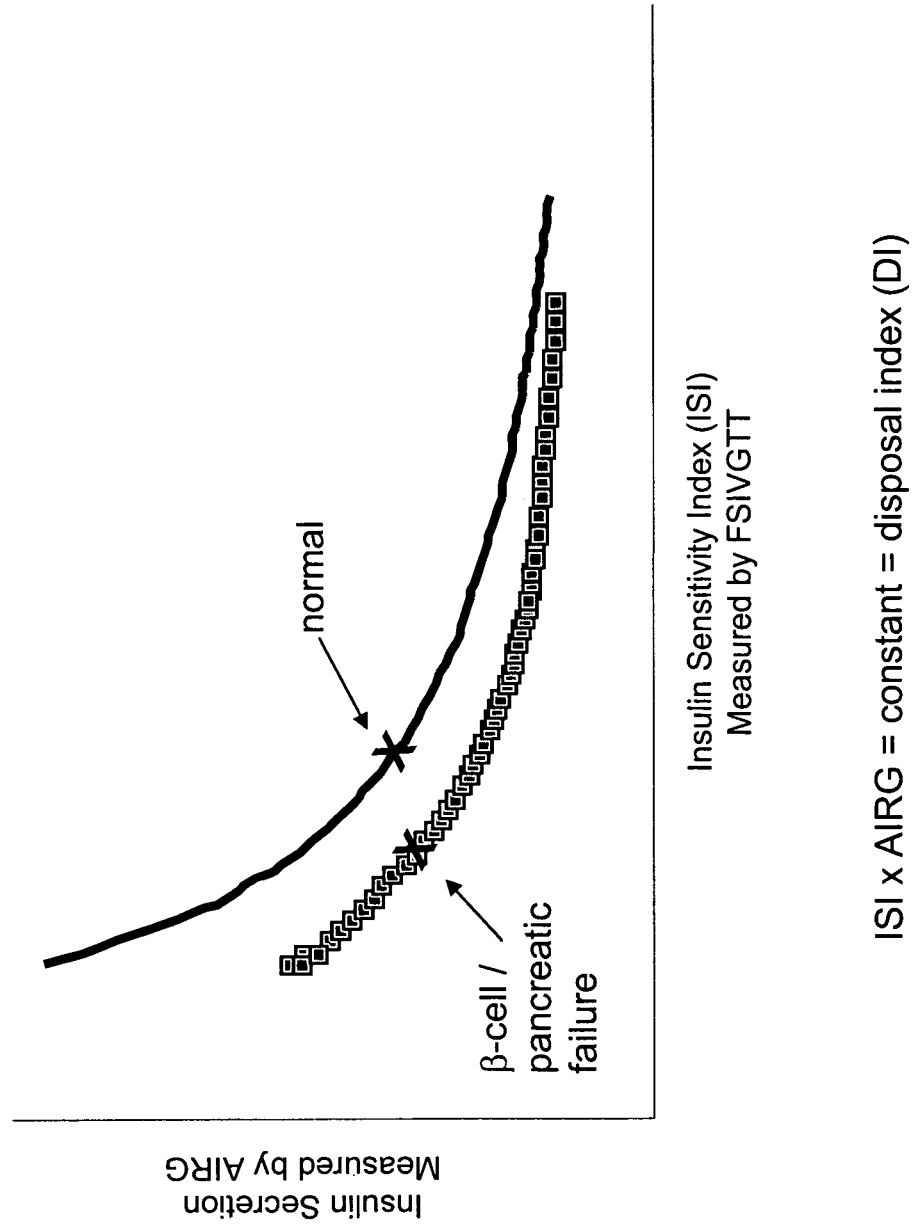
Figure 1: Current views of diabetes pathogenesis – the disposal index

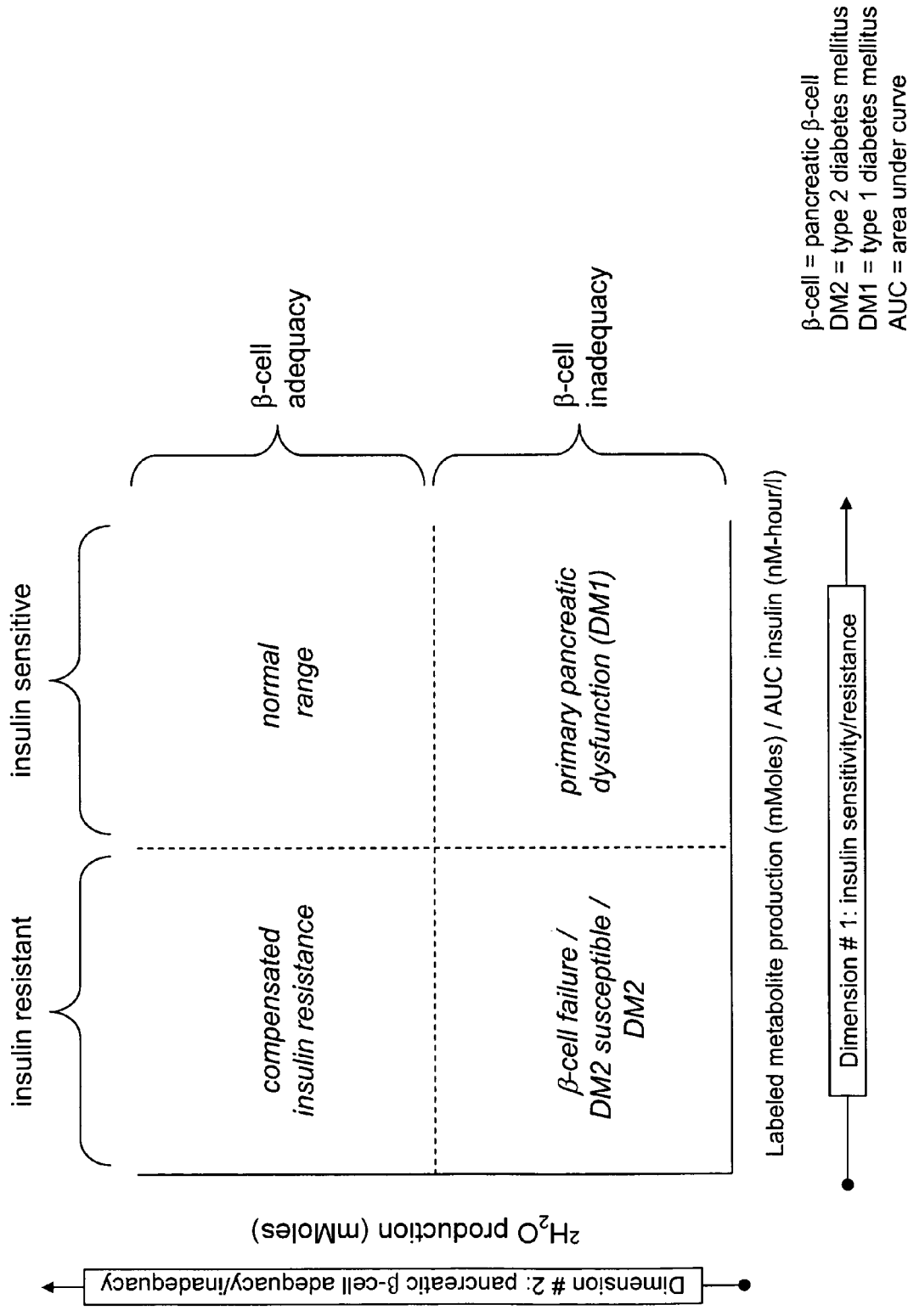
Figure 2: The two critical dimensions of diabetes pathogenesis

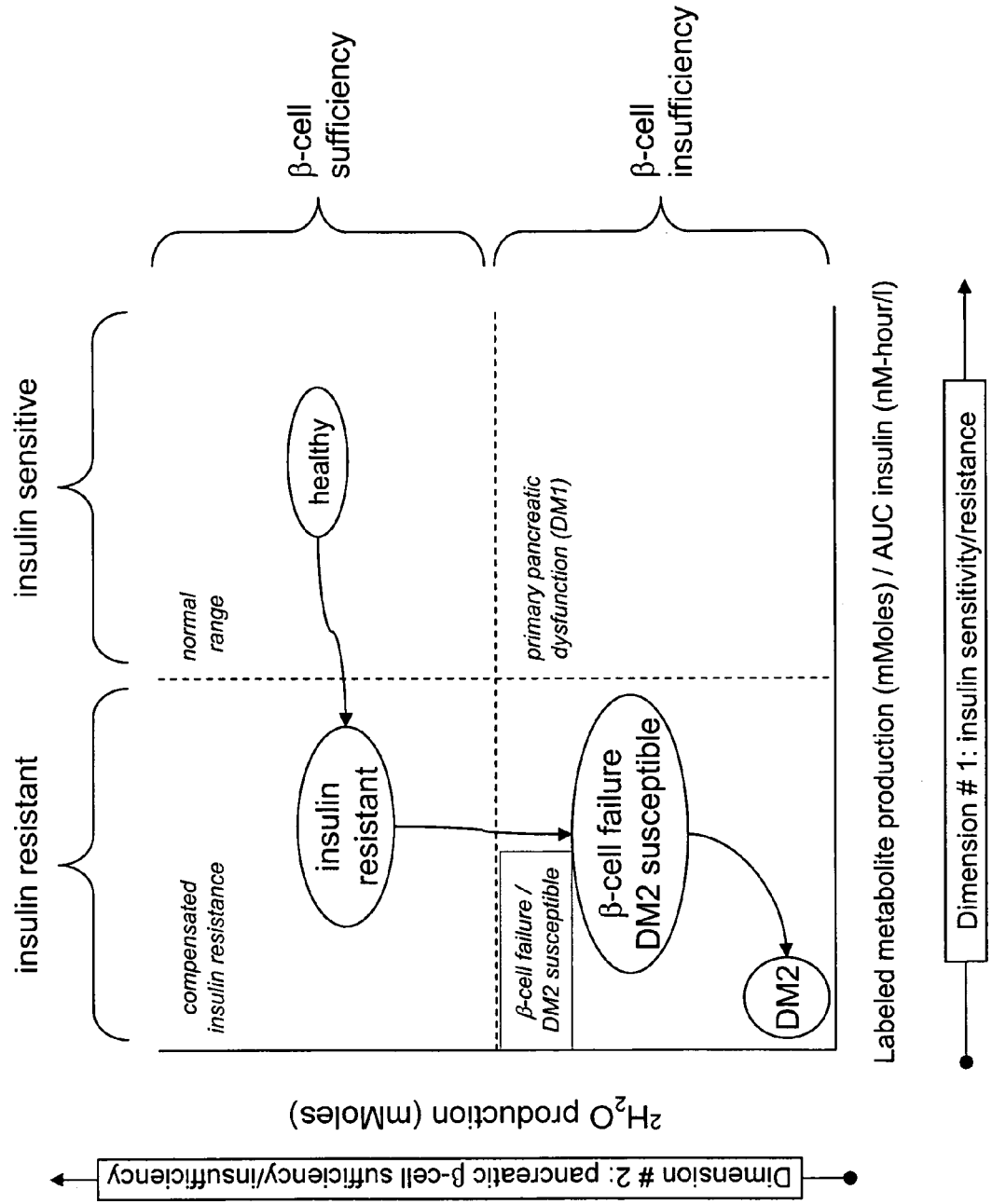
Figure 3: the natural history of type II diabetes (DM2)

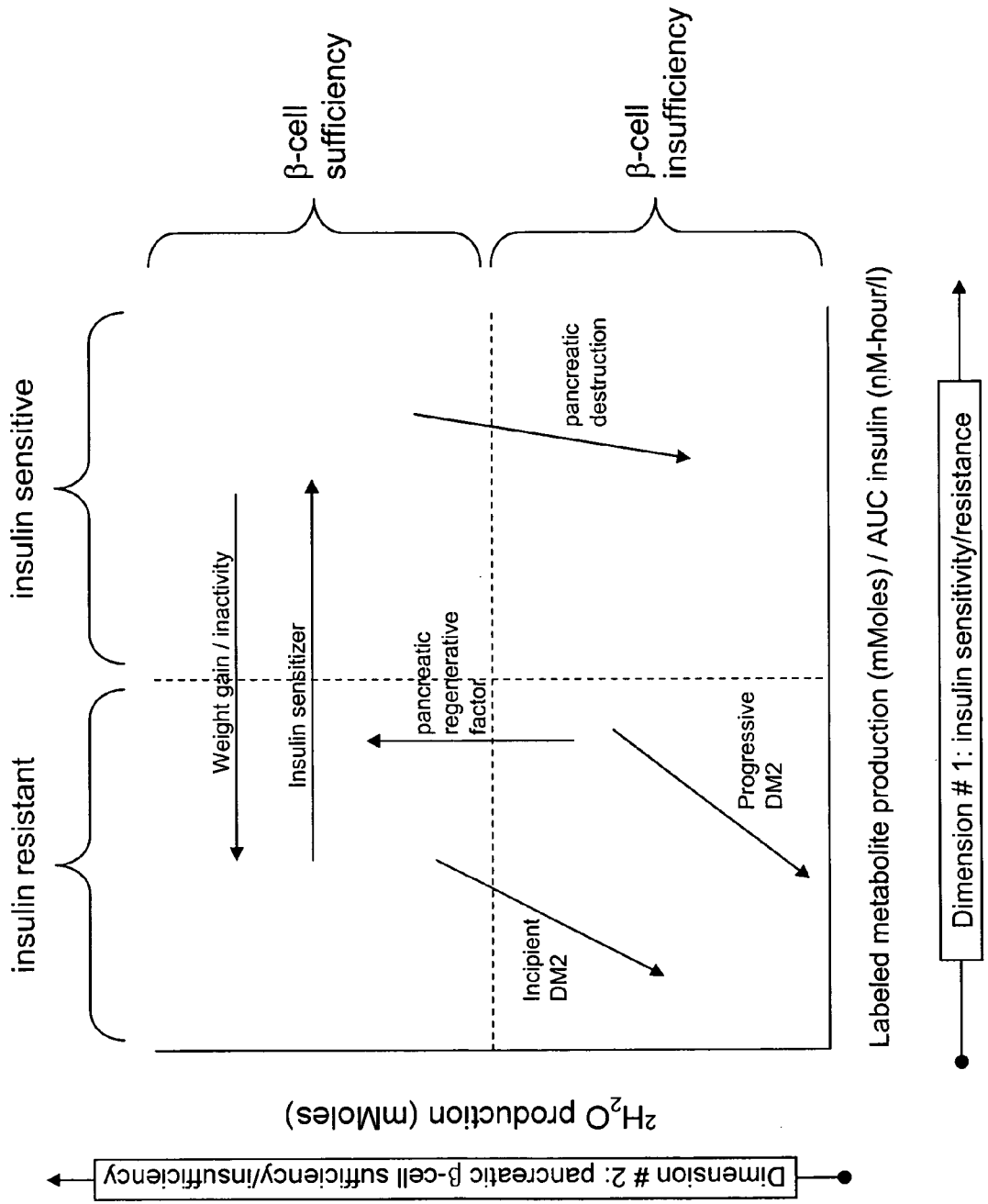
Figure 4: disease transitions in diabetes progression and treatment

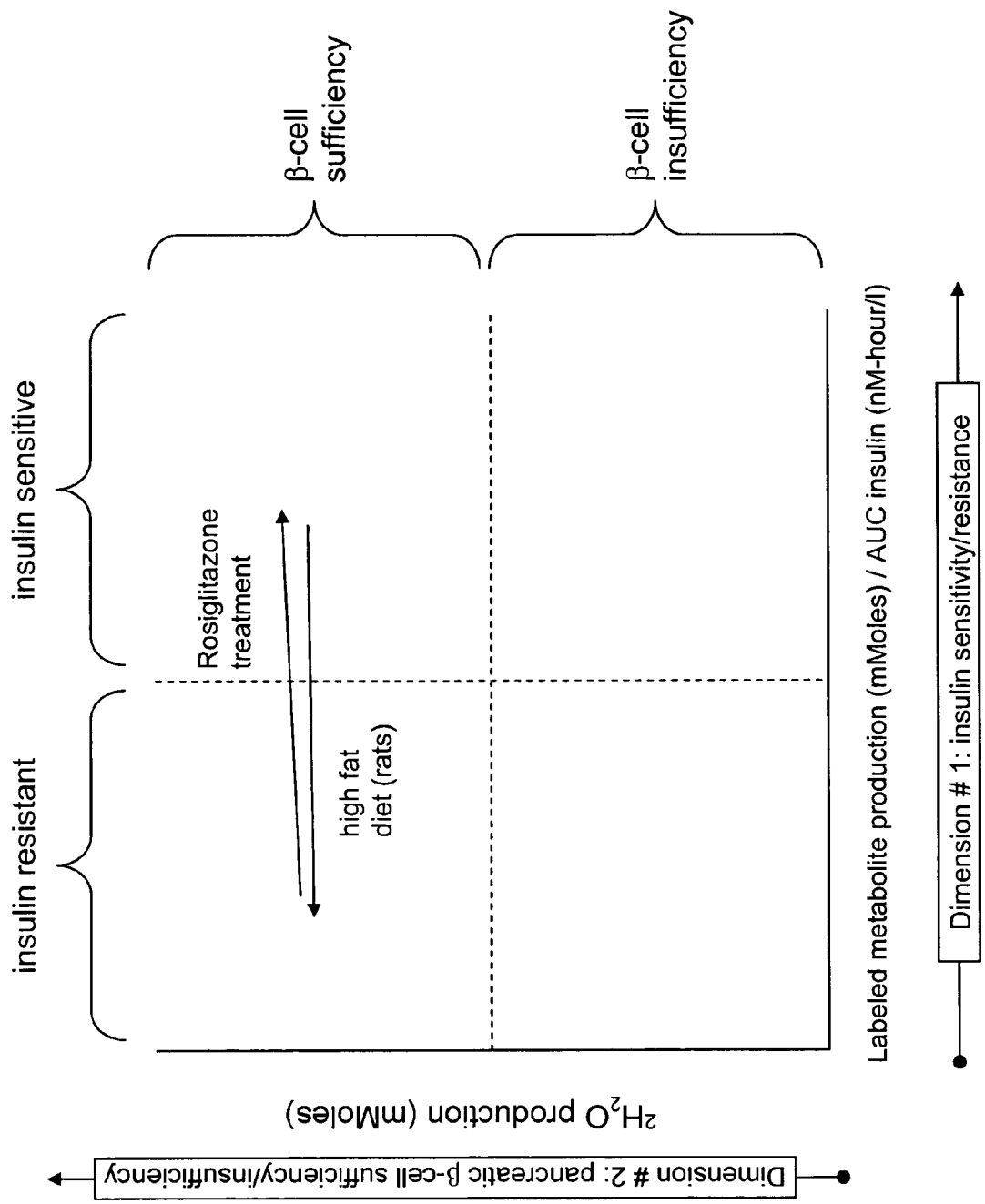
Figure 5: disease transitions in animal models of diabetes

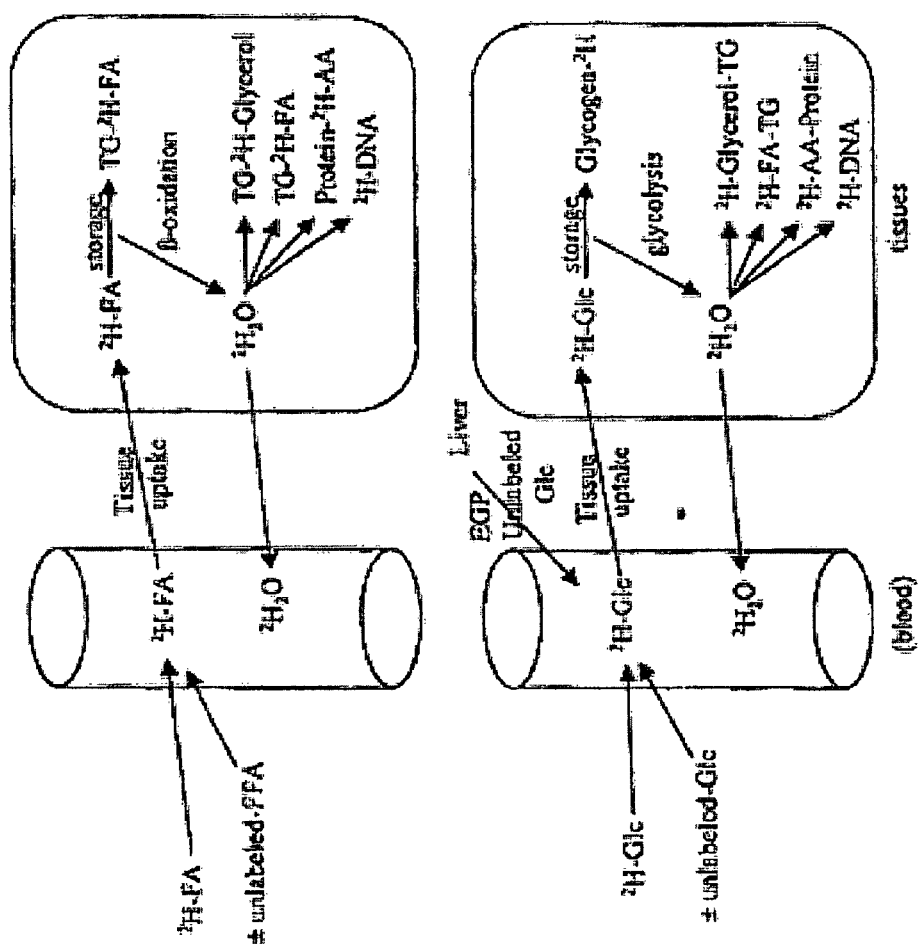
Figure 6: the fates of $^2$H-labeled glucose and fatty acids

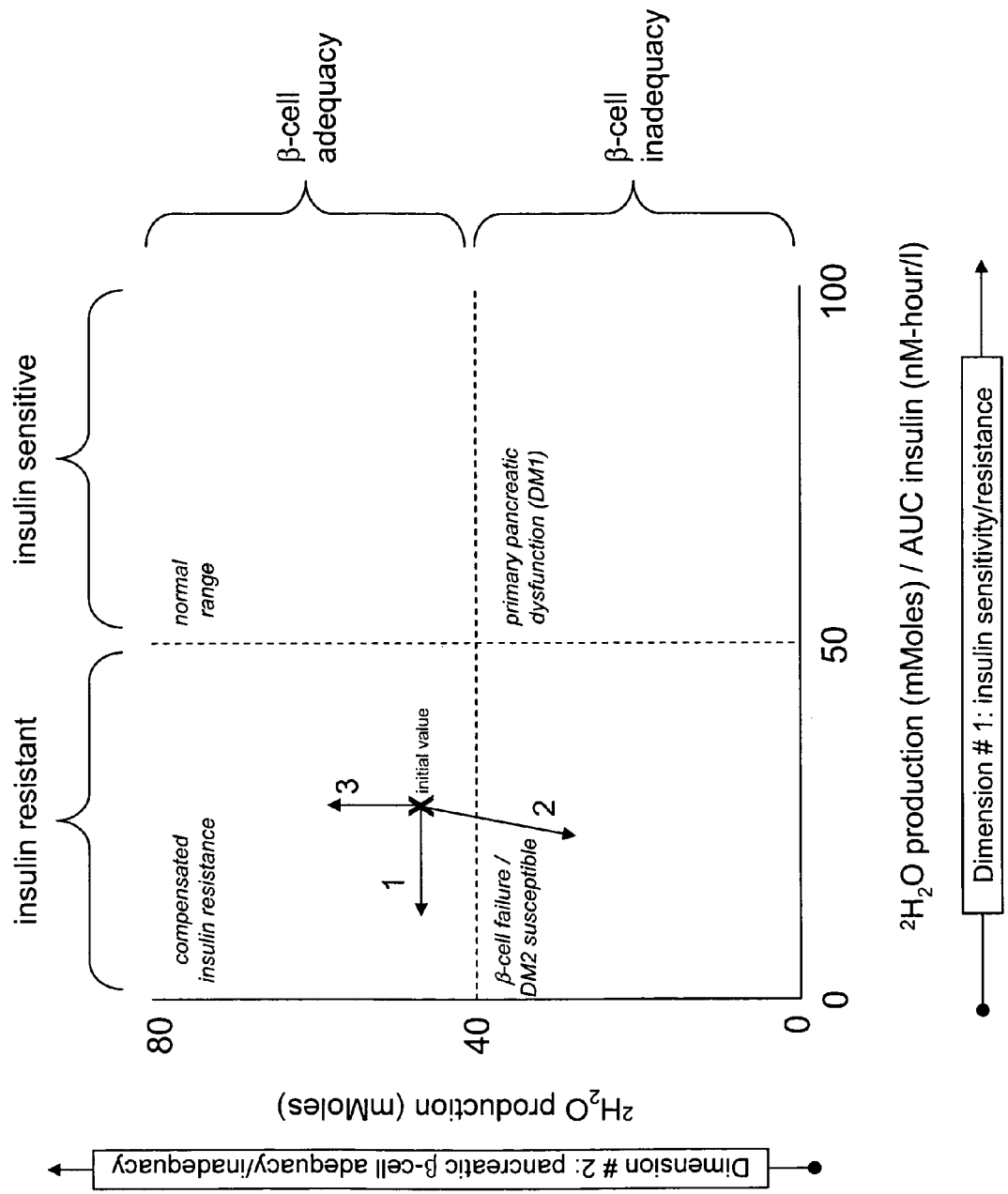
Figure 7: longitudinal monitoring of a human subject

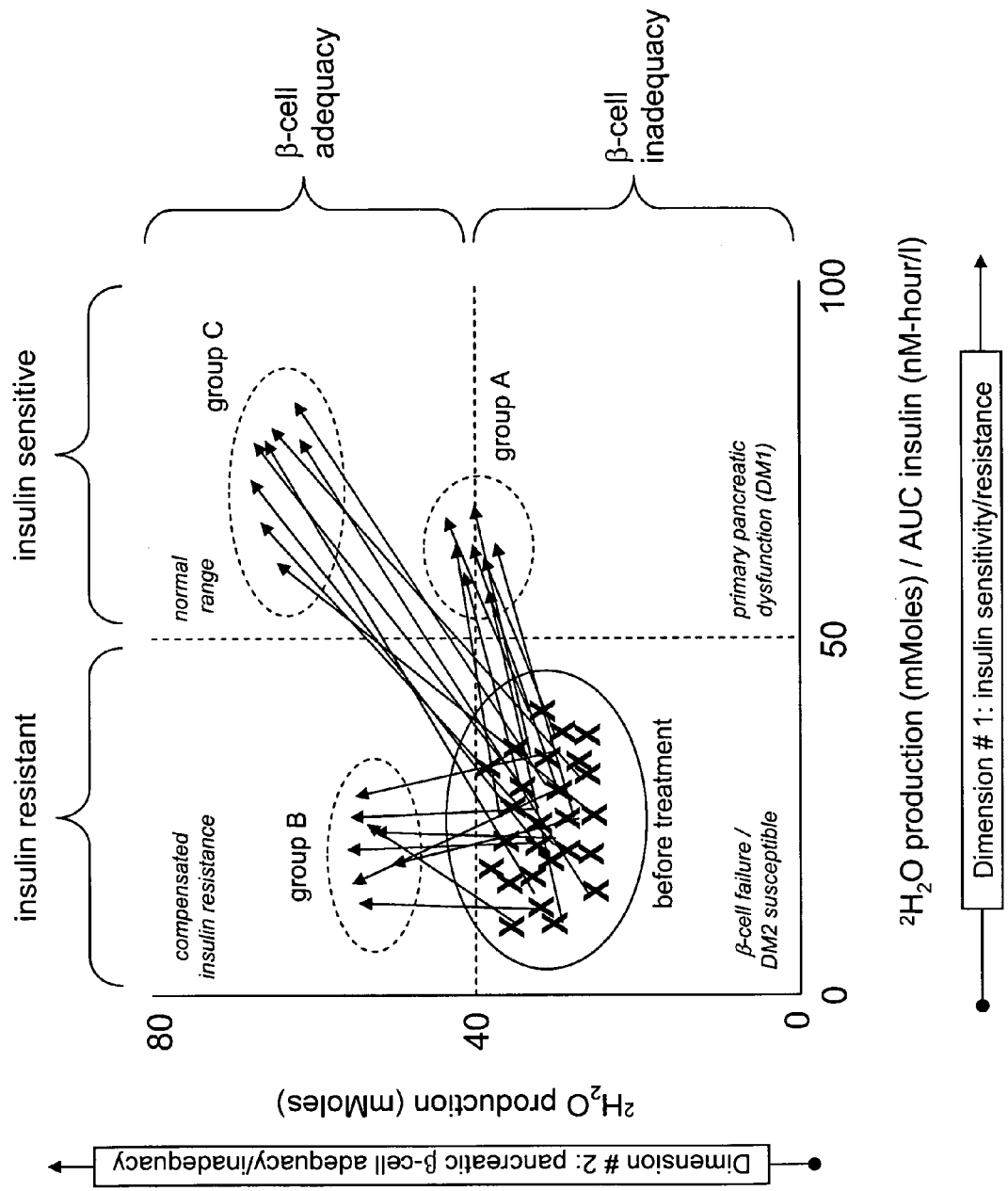

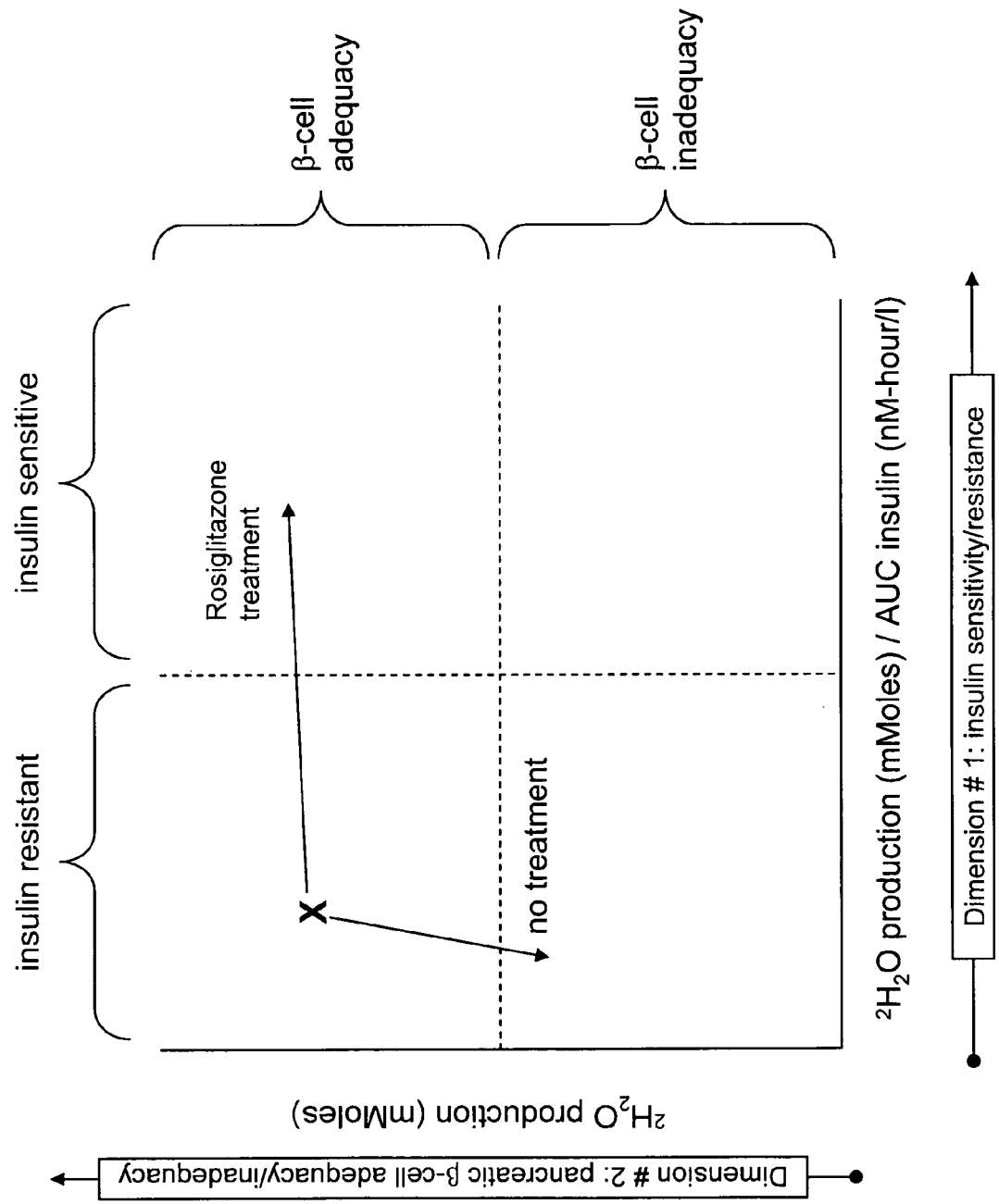
Figure 9: drug evaluation in Zucker diabetic fatty rats

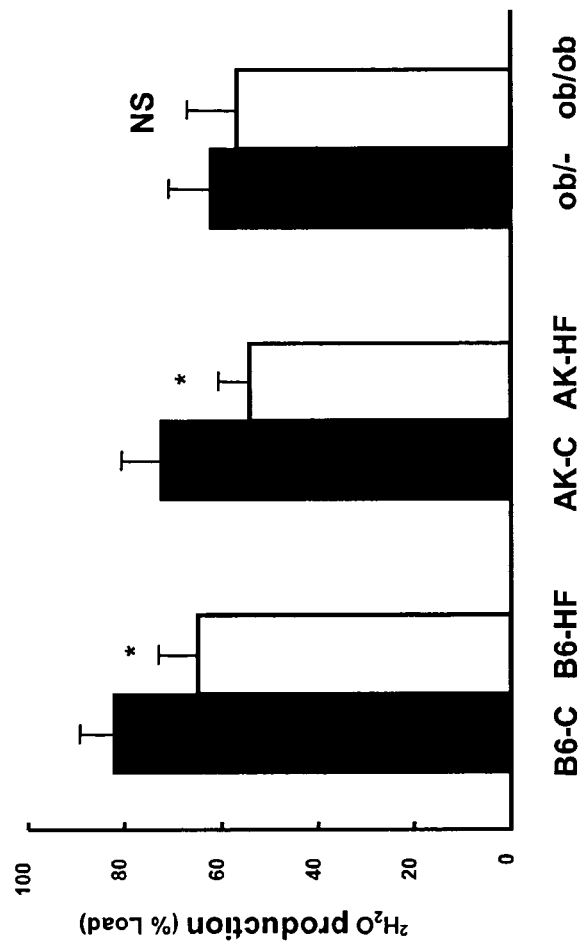
Figure 10: absolute $^2H_2O$ production in animal models of insulin resistance.

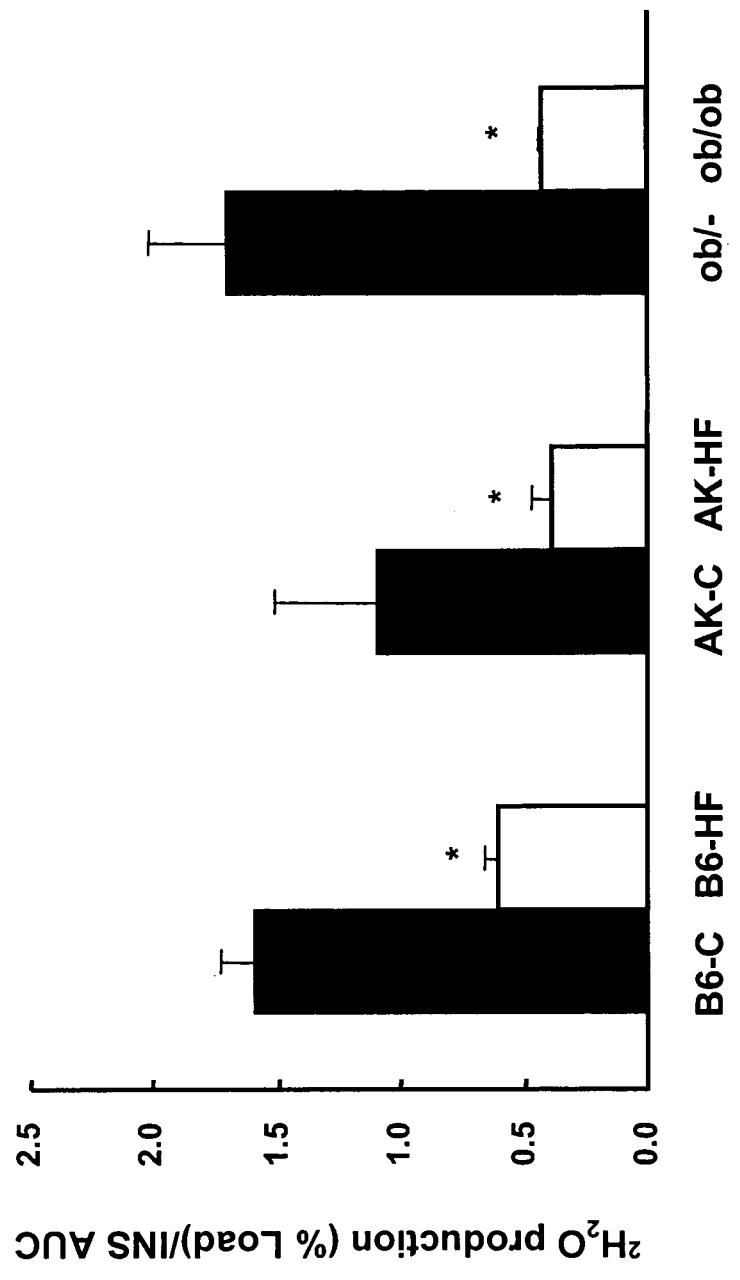
Figure 11: absolute $^2H_2O$ production/insulin AUC in animal models of insulin resistance.

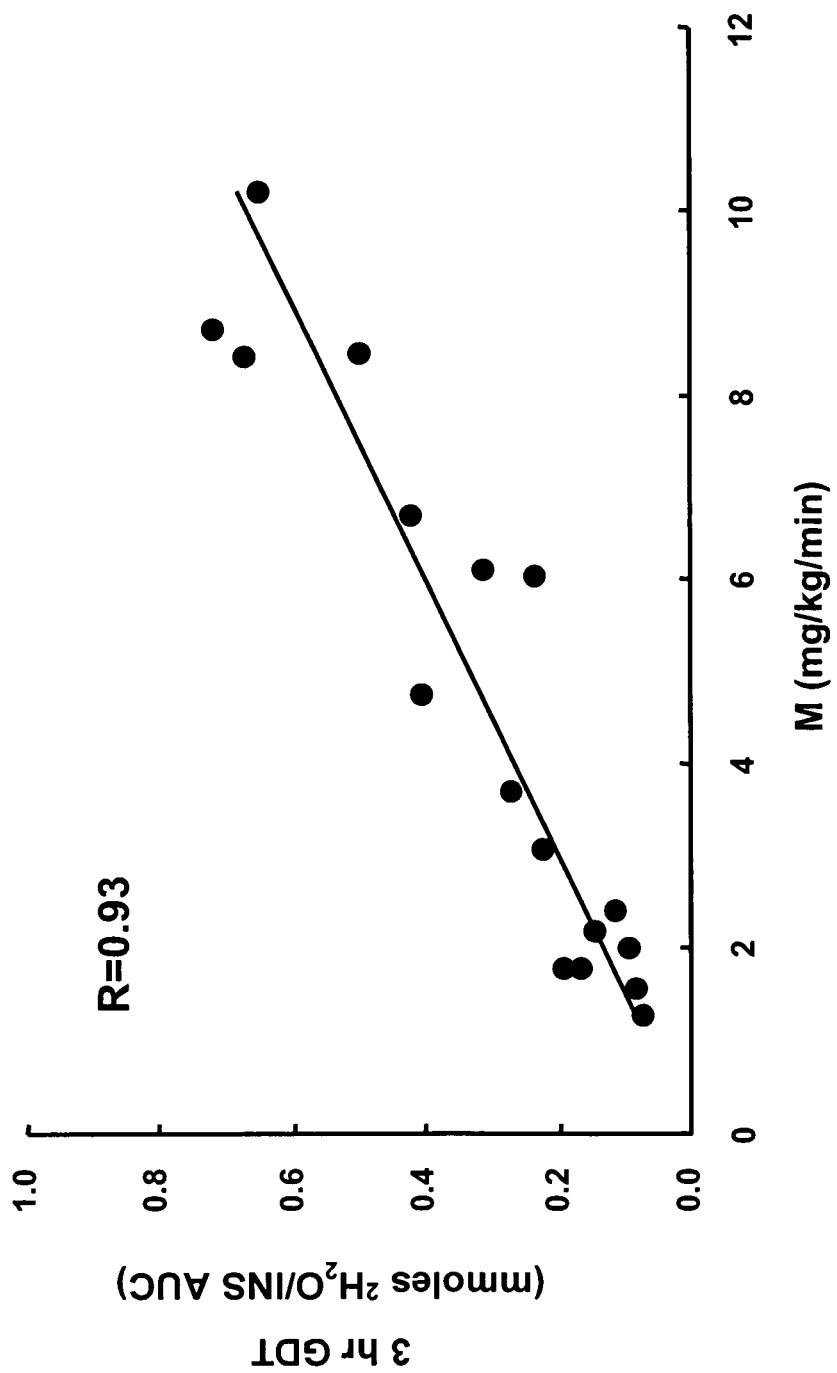
Figure 12: correlation of $^2H_2O$/INS AUC with hyperinsulinemic glucose clamp

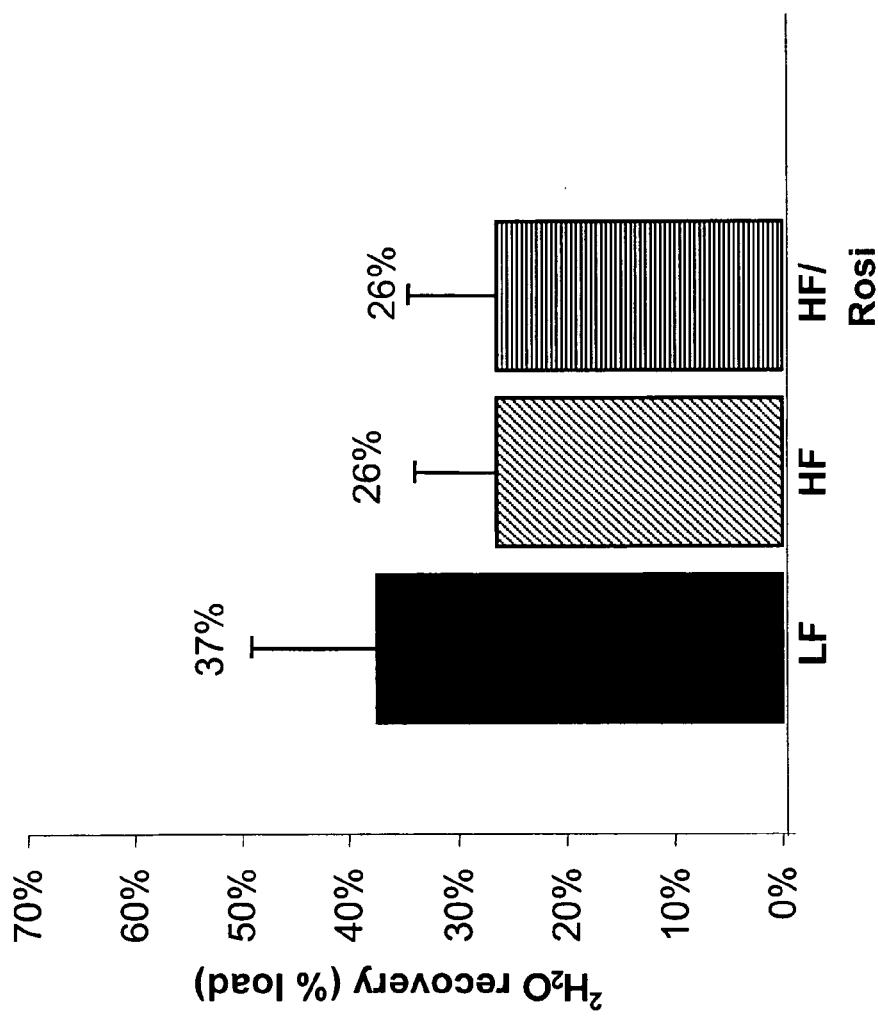
Figure 13: Absolute $^2H_2O$ production after 4 weeks of rosiglitazone (Rosi) treatment following 4-week lead-in with high-fat (HF) diet in SD rats

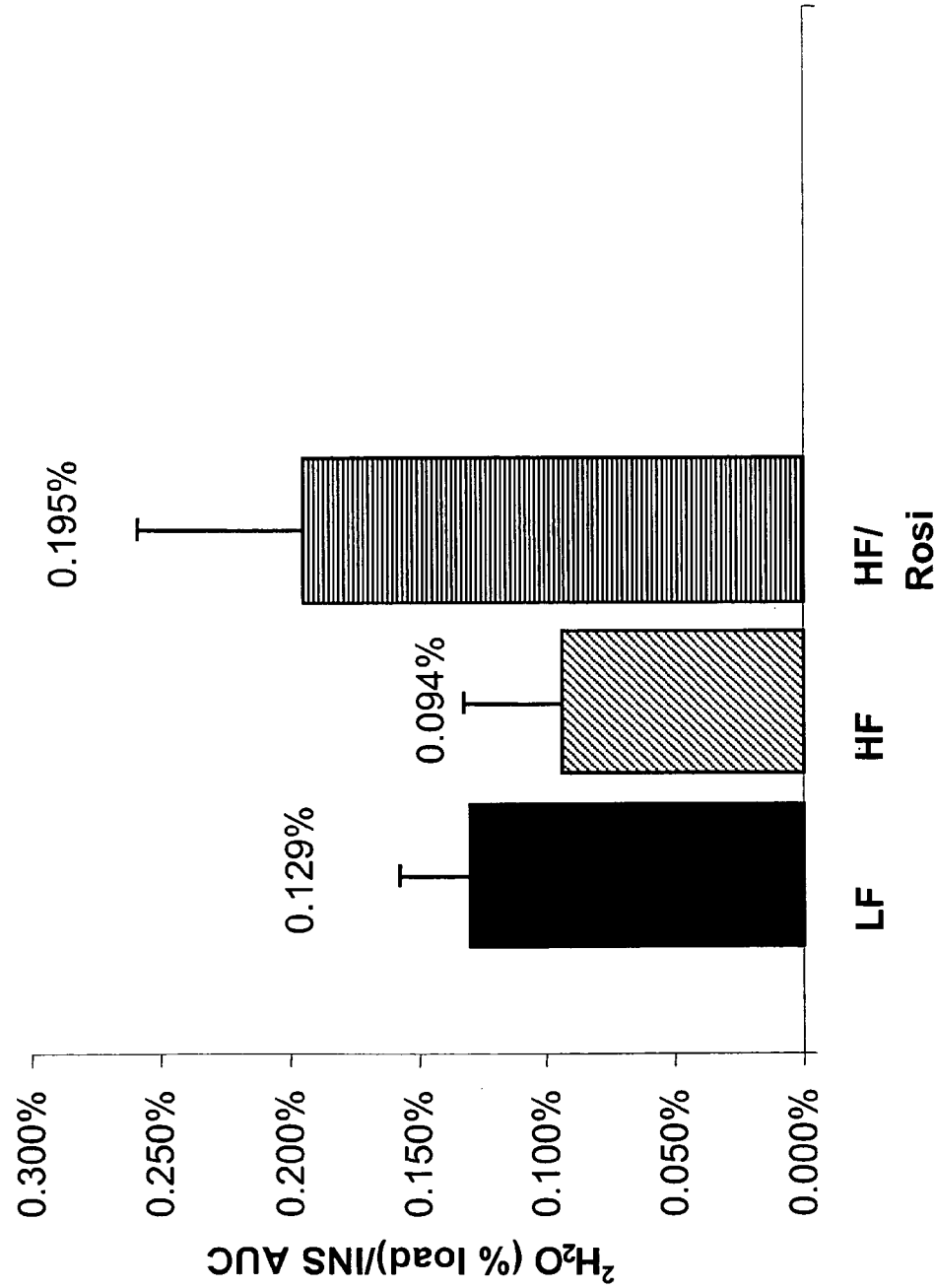
Figure 14: $^2H_2O$ (%load) /INS AUC after 4 weeks of rosiglitazone treatment following 4-week lead-in with high-fat diet in SD rats

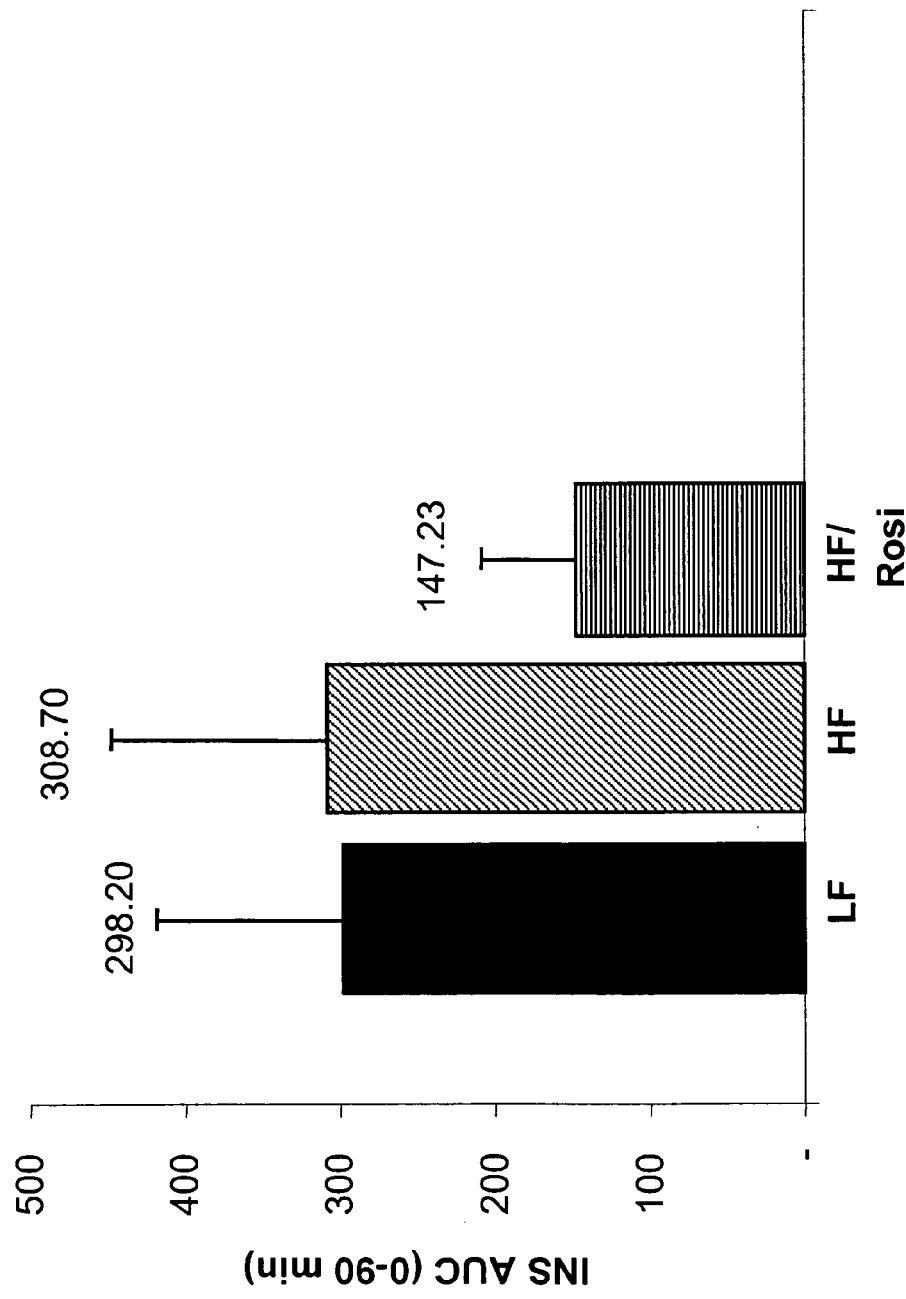
Figure 15: Insulin AUC after after 4 weeks of rosiglitazone (Rosi) treatment following 4-week lead-in with high-fat diet in SD rats

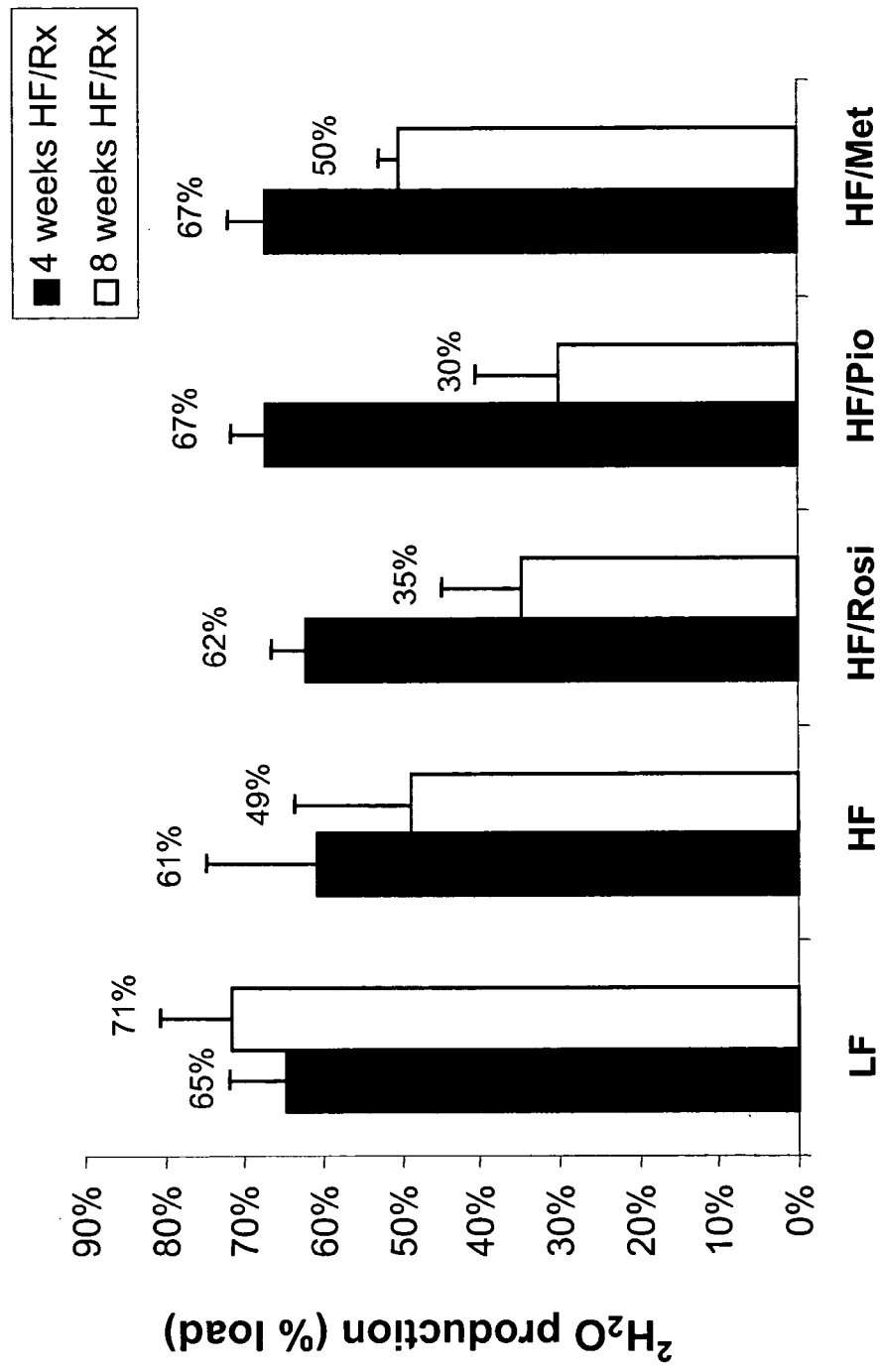
Figure 16: Absolute $^2H_2O$ production after drug treatment following 4-week lead-in with high-fat diet in AKR mice

MONITORING TWO DIMENSIONS OF DIABETES PATHOGENESIS

CROSS-REFERENCE TO RELATED APPLICATION

This application claims the benefit of U.S. Provisional Application No. 60/689,612, filed Jun. 10, 2005, which is hereby incorporated by reference in its entirety.

BACKGROUND OF THE INVENTION

The present application relates to the field of diabetes mellitus (DM). In particular, methods for determining separately or concurrently with a simple, minimally invasive test the presence of tissue insulin resistance and/or the adequacy of pancreatic beta-cell response or compensation in an individual and therefore the individual's susceptibility to developing DM type 2 (DM2) or progressing to more advanced DM2, are described.

The current pathogenic model of type 2 diabetes mellitus (DM2) invokes a two-step process: (1) Insulin resistance (i.e., reduced sensitivity of tissues to the actions of insulin); and (2) Pancreatic beta-cell failure (i.e., insufficient secretion of insulin to compensate for insulin resistance). This model explains numerous empirical observations in the field of DM including:

a) The high predictive power of gestational diabetes (GDM) for subsequent permanent DM2. Pregnancy causes insulin resistance in all women (due to the high levels of progesterone). The inability to increase pancreatic insulin secretion for three months to compensate for insulin resistance, manifested by subsequent development of GDM, therefore predicts failure of the pancreas to compensate and the ultimate development of DM2 when long-standing insulin resistance occurs associated with obesity, aging and sedentary life-style.

b) The observation that only 25-30% of obese (insulin resistant) people will develop DM2. The remaining individuals maintain compensated (hyperinsulinemic) insulin resistance and do not develop DM2. Thus, two lesions are required for the development of DM2 (insulin resistance and pancreatic insufficiency).

c) The natural history of blood insulin concentrations in the progression of obesity to DM2. Insulin concentrations initially rise above normal levels, then fall to normal or low levels, as DM2 emerges.

d) The observation that insulin-sensitizing interventions can prevent progression of pre-diabetes to diabetes. Reducing insulin resistance by exercise or metformin therapy has been shown to improve pancreatic insulin secretion and to prevent progression to DM2.

e) The observation that progression of long-standing DM2, in the United Kingdom Prospective Diabetes Study (UKPDS), for example, involves mainly worsening of beta-cell function, not worsening of insulin resistance. This study showed that patients with long-standing DM2 require more and more drugs to maintain good diabetic control over time, primarily because of worsening insulin secretion, not changes in insulin resistance.

Implications for Diagnostic Monitoring and Drug Testing

Accordingly, full characterization of susceptibility to DM2 or progression along the pathway to DM2 requires information about those two elements or dimensions (insulin resistance and pancreatic beta-cell compensation) involved in the pathogenesis of DM2.

Bergman and others have proposed tests to assess both dimensions. The Frequently Sampled IV Glucose Tolerance Test (FS IVGTT) measures the insulin sensitivity index (ISI) and the acute insulin response to glucose (AIRG), and calculates the adequacy of beta-cell response from these two measured parameters. This method has been extensively used in humans at risk for developing diabetes and has supported the model (Kahn et al, Wyeth et al, see references infra) shown in FIG. 1. The central concept is that a hyperbolic relationship exists between tissue insulin resistance and pancreatic insulin secretion. As insulin sensitivity (ISI) falls, AIRG should rise, so that the product of ISI×AIRG (termed the disposition index or DI) should remain constant (FIG. 1, black line). DI therefore represents a calculated measure of the adequacy of pancreatic compensation to insulin resistance, or an indirect measure of beta-cell sufficiency in the face of insulin resistance. Accordingly, individuals who fail to maintain constancy of DI as ISI falls (gray line in FIG. 1)—i.e., do not fall on the expected hyperbolic curve of ISI vs. AIRG (black line in FIG. 1)—are considered to be showing evidence of pancreatic beta-cell insufficiency.

Investigators have shown that such individuals, whose DI is not maintained in the face of reduced ISI, indeed appear to be at higher risk of developing DM2. Moreover, failure to maintain constant DI is a heritable trait within families at different risks for DM2. DI has therefore been proposed as a means of identifying those insulin resistant individuals who are highly susceptible to developing DM2.

The FS IVGTT is problematic as a test, however, and is much too invasive and complicated to be used in clinical diagnostics, for the following reasons: (1) The placement of an intravenous line is required; (2) multiple blood draws according to an exactly timed protocol are required (e.g., every 1-2 minutes for 20 minutes, then follow-ups through 2 hours); (3) sterile iv glucose must be injected; (4) a drug (tolbutamide) must be injected iv at exactly 20 minutes after iv glucose (carrying some risk and the need for medical supervision) (5) multiple laboratory tests for glucose and insulin concentrations must be sent; and (6) a computerized calculation must be carried out on the data generated. The FS IVGTT is therefore labor-intensive, invasive, costly, difficult to interpret, and to some extent a risky procedure.

Other methods are available for estimating or measuring insulin resistance. These include hyperinsulinemic glucose clamps (considered the "gold standard" for insulin resistance), and the similar steady-state plasma glucose (SSPG) method, the homeostatic model assessment (HOMA), and simple measurement of plasma insulin concentrations. None of these methods can give information about pancreatic beta-cell function or the adequacy of beta-cell compensation for insulin resistance, however. Indeed, the glucose clamp and SSPG methods explicitly control blood insulin to remove the potential confounding influence of pancreatic insulin secretion. There currently are no practically usable tests for measuring or estimating the adequacy of pancreatic beta-cell response to insulin resistance.

It should be apparent that the absence of a simple, practically usable test for identifying individuals who are both insulin resistant and who are exhibiting insufficient pancreatic beta-cell response—and are therefore highly susceptible to developing diabetes or to worsening of existing diabetes—is a major limitation in the field of diabetes. The present emergence in diabetic therapeutic research of agents that may increase pancreatic beta-cell proliferation and function makes the absence of an outcome metric for beta-cell adaptive function particularly critical.

BRIEF SUMMARY OF THE INVENTION

Certain embodiments described herein utilize one or more of the following observations:
a) the production of deuterated water from deuterated glucose (hereinafter referred to as "deuterated water production") was remarkably reduced in some models of insulin resistance (e.g., acute high-fat feeding in rats, Zucker diabetic fatty rats, humans with lipodystrophy and some obese hyperinsulinemic human subjects) and that deuterated water production increased in response to administration of insulin-sensitizing therapies (e.g., thiazolidinediones, metformin), but that deuterated water production was not reduced in all models of insulin resistance. Indeed, some chronic models of insulin resistance (Zucker fatty non-diabetic rats, ob/ob mice, some obese hyperinsulinemic human subjects) exhibited normal or near normal deuterated water production (FIG. 10).
b) the correction of deuterated water production for ambient serum insulin concentrations after administration of deuterated glucose, however, resulted in a measure of tissue insulin sensitivity or resistance that was apparent in all models of insulin resistance tested (FIG. 11), and increased in response to insulin-sensitizing therapies. Deuterated water production divided by insulin area under the curve ($^2H_2O$/INS AUC) thereby reflects the response of tissues to blood insulin and reveals the presence of reduced insulin sensitivity.
c) the insulin-corrected deuterated water production ($^2H_2O$/INS AUC) correlated extraordinarily well with the "gold standard" for measuring insulin resistance (the hyperinsulinemic glucose clamp) in normal and obese humans (FIG. 12). Thus, the $^2H_2O$/INS AUC measurement was validated as a very accurate measure of tissue insulin sensitivity or resistance.
d) animal models of insulin resistance that demonstrated low corrected deuterated water production ($^2H_2O$/INS AUC) but normal or near-normal absolute deuterated water production, were strains that have low susceptibility to DM2 (Zucker fat non-diabetic rat and certain high-fat fed mouse strains). In contrast, animal models exhibiting both low $^2H_2O$/INS AUC and low absolute deuterated water production were strains on the pathway to, or already in, the state of DM2 (Zucker diabetic fatty rats, and other high-fat fed mouse strains). Accordingly, the maintenance of normal absolute heavy water production in the face of insulin resistance was highly informative—"normal" heavy water production in this setting represented sufficiency (adequacy) of the pancreatic beta-cell response to the insulin resistance present. Below normal heavy water production in the face of reduced $^2H_2O$/INS AUC (insulin resistance), in contrast, revealed insufficiency (inadequacy) of the pancreatic beta-cell compensation.
e) These discoveries therefore signified that both dimensions of the DM2 pathogenic model—insulin sensitivity/resistance and adequacy/inadequacy of pancreatic beta-cell response—can be measured through a single test, as described herein, with inclusion of insulin concentrations. Full characterization of DM2 susceptibility and progression is thereby enabled through a simple, easily performed and widely usable test.

In one aspect described herein is a method for determining pancreatic β-cell sufficiency having the steps of: a) administering to a subject isotope-labeled sugars (e.g., $^2H$—labeled sugars) which are metabolized into labeled and unlabeled water; b) obtaining one or more biological samples (e.g., blood) at one or more times from the subject, with at least one sample being obtained after the administration of the isotope-labeled sugars; c) measuring the isotopic content of water in the biological sample(s) to determine the fractional amount of isotope-labeled water in the sample(s); d) determining the total amount of water in the subject; and e) multiplying the fractional amount of isotope-labeled water in the sample(s) by the total amount of water in the subject to determine the total amount of isotope-labeled water in the subject and to determine the β-cell sufficiency in the subject.

In another aspect, herein is described a method for determining pancreatic β-cell sufficiency and insulin sensitivity having the steps of: a) determining the total amount of isotope-labeled water in the subject as described; b) measuring the amount of insulin in the biological sample(s) obtained to determine the total exposure of tissues of the subject to insulin or to determine the insulin production level for the subject; and c) dividing the total amount of isotope-labeled water in the subject by the total exposure of tissues of the subject to insulin or by the insulin production level for the subject to determine insulin resistance in the subject.

In another aspect, the total exposure of tissues of the subject to insulin or the insulin production level for the subject is calculated as an insulin area under the curve (INS AUC).

In another aspect, the isotope-labeled sugars for use with the methods disclosed herein are isotope-labeled glucose, fructose, and/or galactose.

The sugar may be [6,6-$^2H_2$]glucose, [1-$^2H$]glucose, and/or [1,2,3,4,5,6,7-$^2H_7$]glucose.

In yet another aspect, isotope-labeled sugars for use with the methods described herein may be administered orally, by gavage, intraperitoneally, intravenously, and/or subcutaneously.

In another aspect, the additional step of plotting a subject within a graph representing the two dimensions of DM pathogenesis (i.e., insulin sensitivity and adequacy of pancreatic beta-cell response) is performed. The quadrant within which the subject falls reveals his/her clinical condition (specifically: normal range, upper right quadrant; compensated insulin resistance, upper left quadrant; primary pancreatic dysfunction (e.g., DM1), lower right quadrant; and beta-cell failure/high susceptibility to DM2, lower left quadrant—see FIG. 2).

In yet another aspect, a subject is monitored over time through performance of one or more repeat measurements by the methods disclosed herein. Movement within or between quadrants as part of disease development (FIG. 3), can be monitored. Other aspects of change in the two dimensions of DM pathogenesis can also be monitored (FIG. 4). Progression to DM2, progression with existing DM2, response to therapies and other time-dependent changes are monitored in this manner.

In still yet another aspect, animal models of diabetes, obesity, or related conditions are characterized by use of the methods for determining pancreatic β-cell sufficiency and insulin sensitivity, as described herein.

In another aspect, the additional step of plotting one or more animals within a graph representing the two dimensions of DM pathogenesis (i.e., insulin sensitivity and sufficiency of pancreatic beta-cell response) is performed. The quadrant within which the animal falls reveals its condition (specifically: normal range, upper right quadrant; compensated insulin resistance, upper left quadrant; primary pancreatic dysfunction (e.g., DM), lower right quadrant; and beta-cell failure/high susceptibility to DM, lower left quadrant—see FIG. 2).

In yet another aspect, one or more animals are monitored over time through performance of one or more repeat measurements by the methods disclosed herein. Movement within or between quadrants (represented by arrows in FIG. 5), is monitored, or other aspects of change in the two dimensions of DM pathogenesis are monitored. Progression to DM2, progression with existing DM2, response to therapies and other time-dependent changes are monitored in this manner.

In yet another aspect, human or animal subjects are monitored before and after treatment with a candidate agent in order to evaluate the ability of the candidate agent to slow, halt, or reverse the onset or progression of DM2, the onset or progression of insulin resistance, or to otherwise influence either dimension of diabetes pathogenesis.

BRIEF DESCRIPTION OF THE DRAWINGS

FIG. 1 illustrates one aspect of current theories about diabetes pathogenesis. Two factors, insulin sensitivity (ISI) and insulin secretion, contribute to the disposal of glucose. The product of these two factors is a constant, reflecting the utilization of glucose in a healthy subject (represented by the black line). This product is referred to as the disposition index (DI). When diabetes is developing or present, subjects will deviate from this line as they become less able to compensate for insulin resistance by increasing insulin secretion by the pancreatic beta-cells and therefore are less able to metabolize glucose (gray line).

FIG. 2 illustrates the two dimensions of diabetes pathogenesis. The horizontal axis represents insulin sensitivity, and the vertical axis represents pancreatic beta cell sufficiency. Different quadrants of the chart represent different physiologic states, all of which are identifiable by use of the modified glucose disposal test.

FIG. 3 illustrates the natural history of DM2 on the two dimensional pathogenesis chart. Progress from healthy to DM2, as is common in the adult population, is shown.

FIG. 4 illustrates different types of disease transition that can occur in humans. Some treatments (such as insulin sensitizers) can reverse disease transitions and improve the subject's condition.

FIG. 5 illustrates disease transitions that can occur in animal models of diabetes, and after treatment of such animals.

FIG. 6 illustrates the disposal of $^2$H-labeled fatty acids (top) or $^2$H-labeled glucose (bottom). The fate of labeled glucose is of interest in the methods described herein.

FIG. 7 illustrates some potential data from the longitudinal monitoring of a hypothetical insulin resistant human subject over the course of one year. Depending on the progress or treatment of disease, the subject may develop further insulin resistance (arrow #1), may develop pancreatic failure (arrow #2), or may develop improved pancreatic function (arrow #3). Any number of additional outcomes are possible, although only three are illustrated here.

FIG. 8 illustrates the results of a hypothetical clinical trial of a pancreatic regenerative factor alone or in combination with an insulin sensitizing agent as compared to an insulin sensitizing agent alone depicted as an evaluation of candidate therapies.

FIG. 9 illustrates the results of an experiment with insulin resistant high-fat diet fed rats that received either no treatment or treatment with an insulin sensitizer (rosiglitazone) illustrated as a drug evaluation in Zuker diabetic fatty rats.

FIG. 10 illustrates the total $^2$H$_2$O production in different strains of mice when fed either a control diet or a high fat (acute insulin-resistance inducing) diet. Some models of chronic or long-term insulin resistance (ob/ob mice) do not show reduced glucose utilization (absolute $^2$H$_2$O production), even though they are known to be insulin resistant. B6 and AK=two different strains of mice. HF=high fat diet. C=control diet. Ob/–=lean littermates of ob/ob mice. Even in B6 and AK mice, the reduction in $^2$H$_2$O production is slight, indicating a nearly adequate pancreatic compensation to induced insulin resistance.

FIG. 11 illustrates the total $^2$H$_2$O production for the same experimental groups shown in FIG. 10, but divided by the insulin AUC. Severe insulin resistance is now apparent for all animal models.

FIG. 12 illustrates the correlation between the hyperinsulinemic glucose clamp and the $^2$H$_2$O/INS AUC method in humans. The correlation has an R value of 0.93, indicating that the $^2$H$_2$O/INS AUC measurement is comparable in sensitivity to the "gold standard" clamp measurement. Measurements were made on 17 non-diabetic subjects of which 8 are lean control subjects and 9 are subjects with metabolic syndrome.

FIG. 13 illustrates the total $^2$H$_2$O recovery (i.e. absolute $^2$H$_2$O production) in rats fed a HF (high fat) or LF (low fat) diet for 4 weeks followed by 4 weeks of treatment with or without rosiglitazone (insulin sensitizer). HF diet reduced total $^2$H$_2$O production which was not increased by rosiglitazone treatment.

FIG. 14 illustrates the $^2$H$_2$O/INS AUC (insulin sensitivity) of rats fed a HF (high fat) or LF (low fat) diet for 4 weeks followed by 4 weeks of treatment with or without rosiglitazone. $^2$HO/INS AUC (insulin sensitivity) increased in the HF population receiving rosiglitazone treatment. Combined with data in FIG. 13, this result suggests that HF diet resets the pancreas to secrete insufficient insulin. Improved insulin sensitivity then maintains the same glucose utilization, but at lower insulin concentrations.

FIG. 15 illustrates the Insulin AUC (0-90 min) of rats fed a HF (high fat) or LF (low fat) diet for 4 weeks followed by 4 weeks of treatment with or without rosiglitazone. Insulin concentrations in rats receiving rosiglitazone treatment decreased.

FIG. 16 illustrates $^2$H$_2$O production in mice fed a HF (high fat) or LF (low fat) followed by a 4 week treatment with or without insulin sensitizing agents.

DETAILED DESCRIPTION

Introduction

Methods for determining concurrently the state of two dimensions of DM pathogenesis in a subject—insulin sensitivity/resistance and/or adequacy/inadequacy of pancreatic beta-cell response are described herein.

In one aspect, the methods disclosed herein represent a reliable measure of tissue insulin resistance in a subject (isotope-labeled metabolite production/INS AUC) concurrently with a reliable measure of the adequacy of pancreatic beta-cell response (absolute isotope-labeled metabolite production).

In another aspect, the methods disclosed herein represent a reliable measure of tissue insulin resistance in an experimental animal concurrently with a reliable measure of the adequacy of pancreatic beta-cell response in an experimental animal.

General Techniques

The practice of the present methods will employ, unless otherwise indicated, conventional techniques of phlebotomy, medicine, clinical chemistry, organic chemistry, analytical chemistry, molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8); J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1146-E1162, 1999). Additionally, the methods disclosed in US Patent Application Publication 2004/0115131 A1, naming Marc Hellerstein as the inventor, may also find use in the methods described herein. Furthermore, procedures employing commercially available assay kits and reagents will typically be used according to manufacturer-defined protocols unless otherwise noted. These references are hereby incorporated by reference, in their entirety.

Definitions

Unless otherwise defined, all terms of art, notations and other scientific terminology used herein are intended to have the meanings commonly understood by those of skill in the art to which the methods described herein pertain. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, Mass isotopomer distribution analysis at eight years: theoretical, analytic and experimental considerations by Hellerstein and Neese (Am J Physiol 276 (Endocrinol Metab. 39) E1146-E1162, 1999). As appropriate, procedures involving the use of commercially available kits and reagents are generally carried out in accordance with manufacturer defined protocols and/or parameters unless otherwise noted.

"Molecular flux rates" refers to the dynamic flow or rate of synthesis and/or breakdown of molecules within a cell, tissue, or organism. "Molecular flux rates" also refers to a molecule's input into or removal from a pool of molecules, and is therefore synonymous with the flow into and out of said pool of molecules.

"Metabolic pathway" refers to any linked series of two or more biochemical steps in a living system (i.e., a biochemical process), the net result of which is a chemical, spatial or physical transformation of a molecule or molecules. Metabolic pathways are defined by the direction and flow of molecules through the biochemical steps that comprise the pathway. Molecules within metabolic pathways can be of any biochemical class, e.g., including but not limited to lipids, proteins, amino acids, carbohydrates, nucleic acids, polynucleotides, porphyrins, glycosaminoglycans, glycolipids, intermediary metabolites, inorganic minerals, ions, etc.

"Flux rate through a metabolic pathway" refers to the rate of molecular transformations through a defined metabolic pathway. The unit of flux rates through pathways is chemical mass per time (e.g., moles per minute, grams per hour). Flux rate through a pathway optimally refers to the transformation rate from a clearly defined biochemical starting point to a clearly defined biochemical end-point, including all the stages in between in the defined metabolic pathway of interest.

"Isotopes" refer to atoms with the same number of protons and hence of the same element but with different numbers of neutrons (e.g., $^1H$ vs. $^2H$ or D).

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers). "Isotope-labeled water" includes water labeled with one or more specific heavy isotopes of either hydrogen or oxygen. Specific examples of isotope-labeled water include $^2H_2O$, $^3H_2O$, and $H_2^{18}O$.

"Food additive" includes, but is not limited to, organoleptic agents (i.e., those agents conferring flavor, texture, aroma, and color), preservatives such as nitrosamines, nitrosamides, N-nitroso substances and the like, congealants, emulsifiers, dispersants, fumigants, humectants, oxidizing and reducing agents, propellants, sequestrants, solvents, surface-acting agents, surface-finishing agents, synergists, pesticides, chlorinated organic compounds, any chemical ingested by a food animal or taken up by a food plant, and any chemical leaching into (or otherwise finding its way into) food or drink from packaging material. The term is meant to encompass those chemicals which are added into food or drink products at some step in the manufacturing and packaging process, or find their way into food by ingestion by food animals or uptake by food plants, or through microbial byproducts such as endotoxins and exotoxins (pre-formed toxins such as botulinin toxin or aflatoxin), or through the cooking process (such as heterocyclic amines, e.g., 2-amino-3-methyllimidazo[4,5-f]quinolone), or by leaching or some other process from packaging material during manufacturing, packaging, storage, and handling activities.

"Industrial chemical" includes, but is not limited to, volatile organic compounds, semi-volatile organic compounds, cleaners, solvents, thinners, mixers, metallic compounds, metals, organometals, metalloids, substituted and non-substituted aliphatic and acyclic hydrocarbons such as hexane, substituted and non-substituted aromatic hydrocarbons such as benzene and styrene, halogenated hydrocarbons such as vinyl chloride, aminoderivatives and nitroderivatives such as nitrobenzene, glycols and derivatives such as propylene glycol, ketones such as cyclohexanone, aldehydes such as furfural, amides and anhydrides such as acrylamide, phenols, cyanides and nitrites, isocyanates, and pesticides, herbicides, rodenticides, and fungicides.

"Environmental pollutant" includes any chemical not found in nature or chemicals that are found in nature but artificially concentrated to levels exceeding those found in nature (at least found in accessible media in nature). So, for example, environmental pollutants can include any of the non-natural chemicals identified as an occupational or industrial chemical yet found in a non-occupational or industrial setting such as a park, school, or playground. Alternatively, environmental pollutants may comprise naturally occurring chemicals such as lead but at levels exceeding background (for example, lead found in the soil along highways deposited by the exhaust from the burning of leaded gasoline in automobiles). Environmental pollutants may be from a point source such as a factory smokestack or industrial liquid discharge into surface or groundwater, or from a non-point source such as the exhaust from cars traveling along a highway, the diesel exhaust (and all that it contains) from buses traveling along city streets, or pesticides deposited in soil from airborne dust originating in farmlands. As used herein, "environmental contaminant" is synonymous with "environmental pollutant."

"Exact mass" refers to mass calculated by summing the exact masses of all the isotopes in the formula of a molecule (e.g., 32.04847 for CH3NHD).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence a the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as M0; for most organic molecules, this is the species containing all $^{12}C$, $^1H$, $^{16}O$, $^{14}N$, etc. Other mass isotopomers are distinguished by their mass differences from M0 (M1, M2, etc.). For a given mass isotopomer, the location or position of isotopes within the molecule is not specified and may vary (i.e., "positional isotopomers" are not distinguished).

"Mass isotopomer envelope" refers to the set of mass isotopomers comprising the family associated with each molecule or ion fragment monitored.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonymously with the term "mass isotopomer pattern."

"Monoisotopic mass" refers to the exact mass of the molecular species that contains all $^1H$, $^{12}C$, $^{14}N$, $^{16}O$, $^{32}S$, etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as m0 and the masses of other mass isotopomers are identified by their mass differences from m0 (m1, m2, etc.).

By "derivatize", "derivatizing", "derivatization", "hydrolysis and derivatization", in the context of the current methods, is meant the process of preparing samples for GC/MS analysis. This preparation can be performed on isolated biomolecules, cells, complex samples, or other samples or molecules and the specific process varies depending on the pathway being analyzed. Such preparation involves multiple procedures, each with many steps, and usually ends with a "derivatization" procedure. As such, the extended process of sample preparation may occasionally be referred to by these terms, as it is the final procedure. In context, the term may also refer only to this final procedure.

"Isotopically perturbed" refers to the state of an element or molecule that results from the explicit incorporation of an element or molecule with a distribution of isotopes that differs from the distribution that is most commonly found in nature, whether a naturally less abundant isotope is present in excess (enriched) or in deficit (depleted).

By "molecule of interest" is meant any molecule (polymer and/or monomer), including but not limited to, amino acids, carbohydrates, fatty acids, peptides, sugars, lipids, nucleic acids, polynucleotides, glycosaminoglycans, polypeptides, or proteins that are present within a metabolic pathway within a living system. In the context of the present methods, a "molecule of interest" may be a "biomarker" of disease and its flux rate, relative to the flux rate of an unexposed or otherwise healthy subject (i.e., control subject), may represent clinically non-observant or subtle pathophysiological occurrences in a subject of interest that may be-predictive of future disease or injury in the subject of interest. In this manner, comparing the flux rates of one or more biomarkers of interest in a subject of interest with the flux rates of one or more biomarkers of interest in a control subject, will find use in diagnosing the subject of interest with, or evaluating or quantifying the subject of interest's risk in acquiring, a disease of interest. Moreover, such information will find use in establishing a prognosis for a subject of interest having a disease of interest, monitoring the progression of a disease of interest in a subject of interest, or evaluating the therapeutic efficacy of a treatment regimen in a subject of interest having a disease of interest.

"Monomer" refers to a chemical unit that combines during the synthesis of a polymer and which is present two or more times in the polymer.

"Polymer" refers to a molecule synthesized from and containing two or more repeats of a monomer. A "biopolymer" is a polymer synthesized by or in a living system or otherwise associated with a living system.

By "carbohydrate" is meant an aldehyde or ketone derivative of a straight-chain polyhydroxyl alcohol containing at least three carbon atoms. The polyhydroxyl alcohol is primarily (but not exclusively) of the pentahydric and hexahydric alcohol varieties. Carbohydrates are so named because the hydrogen and oxygen are usually in the proportion to form water with the general formula Cn(H2O)n. The most important carbohydrates are the starches, sugars, celluloses and gums. They are classified into mono, di, tri, poly and heterosaccharides. The smallest are monosaccharides like glucose whereas polysaccharides such as starch, cellulose or glycogen can be large and indeterminate in length.

By "sugar" is meant the common name for any crystalline, simple carbohydrate that is an aldehyde or ketone derivative of a polyhydric alcohol. A sugar may be, but need not be, sweet. Sugars are mainly disaccharides like sucrose and monosaccharides like fructose or glucose. The term encompasses monosaccharides, disaccharides, trisaccharides, heterosaccharides, or polysaccharides (which are comprised of monosaccharide residues). Monosaccharides include glucose (both D-glucose and L-glucose), mannose, fructose galactose and sugar derivatives including, but not limited to N-acetylmuramic acid, N-acetylneuraminic acid and other sialic acids, N-acetylmannosamine, glucuronic acid, glucosamine, etc. Polysaccharides include disaccharides such as sucrose, maltose and lactose and longer chain sugar molecules such as starch, glycogen, cellulose, chitin, etc.

By the term "oligosaccharide" is meant a molecule comprised of a few covalently linked monosaccharide monomers.

"Isotope labeled substrate" includes any isotope-labeled precursor molecule that is able to be incorporated into a molecule of interest in a living system. Examples of isotope labeled substrates include, but are not limited to, $^2H_2O$, $^3H_2O$, $^2H$-glucose, $^2H$-labeled organic molecules, $^{13}C$-labeled organic molecules, and $^{14}C$-labeled organic molecules.

"Labeled sugar" refers to a sugar incorporating a stable isotope label such as one or more $^2H$ isotopes.

"Deuterated water" refers to water incorporating a stable isotope label such as one or more $^2H$ isotopes.

"Labeled glucose" refers to glucose labeled with one or more $^2H$ isotopes. Specific examples of labeled glucose or $^2H$-labeled glucose include $[6,6-^2H_2]$glucose, $[1-^2H_1]$glucose, and $[1,2,3,4,5,6-^2H_7]$ glucose.

"Exposing" a living system to a compound such as a chemical entity or entities can be from, but is not limited to, topical application, oral ingestion, inhalation, subcutaneous injection, intraperitoneal injection, intravenous injection, and intraarterial injection, in animals or other higher organisms.

By "therapeutic action" is meant an effect on a biochemical or molecular process (i.e., the flow of molecules through metabolic pathways or networks) that is believed to be responsible for, or contributing in, a causal manner to the initiation, progression, severity, pathology, aggressiveness, grade, activity, disability, mortality, morbidity, disease subclassification or other underlying pathogenic or pathologic feature of one or more diseases wherein said effect is beneficial to health or otherwise contributes to a desirable outcome (e.g., a desirable clinical outcome).

By "action" is meant a specific and direct consequence of an intervention such as the administering of a drug.

By "effect" is meant any consequence, including secondary or tangential, not only of an intervention with a compound but a consequence of a natural occurrence such as the effect a gene exerts when naturally expressed or inhibited.

By "toxic effect" is meant an adverse response by a living system exposed to a compound or combinations or mixtures thereof. A toxic effect can include, for example, end-organ toxicity.

An "individual" is a vertebrate, preferably a mammal, more preferably a human.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

"At least partially identified" in the context of drug discovery and development means at least one clinically relevant pharmacological characteristic of a drug agent (i.e., a "compound") has been identified using one or more of the methods described herein. This characteristic may be a desirable one, for example, increasing or decreasing molecular flux rates through a metabolic pathway that contributes to a disease process, altering signal transduction pathways or cell surface receptors that alter the activity of metabolic pathways relevant to a disease, inhibiting activation of an enzyme and the like. Alternatively, a pharmacological characteristic of a drug agent may be an undesirable one for example, the production of one or more toxic effects. There are a plethora of desirable and undesirable characteristics of drug agents well known to those skilled in the art and each will be viewed in the context of the particular drug agent being developed and the targeted disease. A drug agent can be more than at least partially identified when, for example, several characteristics have been identified (desirable or undesirable or both) that are sufficient to support a particular milestone decision point along the drug development pathway. Such milestones include, but are not limited to, pre-clinical decisions for in vitro to in vivo transition, pre-IND filing go/no go decision, phase I to phase II transition, phase II to phase III transition, NDA filing, and FDA approval for marketing. Therefore, "at least partially" identified includes the identification of one or more pharmacological characteristics useful in evaluating a drug agent in the drug discovery/drug development process. A pharmacologist or physician or other researcher may evaluate all or a portion of the identified desirable and undesirable characteristics of a drug agent to establish its therapeutic index. This may be accomplished using procedures well known in the art.

"Manufacturing a drug agent" in the context of the methods described herein includes any means, well known to those skilled in the art, employed for the making of a drug agent product. Manufacturing processes include, but are not limited to, medicinal chemical synthesis (i.e., synthetic organic chemistry), combinatorial chemistry, biotechnology methods such as hybridoma monoclonal antibody production, recombinant DNA technology, and other techniques well known to the skilled artisan. Such a product may be a final drug agent that is marketed for therapeutic use, a component of a combination product that is marketed for therapeutic use, or any intermediate product used in the development of the final drug agent product, whether as part of a combination product or a single product. "Manufacturing drug agent" is synonymous with "manufacturing a compound."

By "authentic biomarker" is meant a physical, biochemical, or physiologic measurement from or on the organism that represents a true or intended mechanistic target of a compound or a mechanistic event believed to be responsible for, or contributing in, a causal manner to the initiation, progression, severity, pathology, aggressiveness, grade, activity, disability, mortality, morbidity, disease sub-classification or other underlying pathogenic or pathologic feature of one or more diseases. A biomarker may be the target for monitoring the outcome of a therapeutic intervention (i.e., the functional or structural target of a drug agent). As defined herein "authentic biomarker" and "biomarkers" are used interchangeably herein and refer to biochemical processes that are involved in, or are believed to be involved in, the etiology or progression of a disease or disorder. The biochemical process (i.e., the flow of molecules through a targeted metabolic pathway or network) is the focus of analysis (as disclosed herein) since it is the underlying changes of the biochemical process (i.e., molecular flux rates) that may be the significant or authentic target for treatment or diagnostic monitoring of the disease or disorder.

By "surrogate biomarker" is meant a physical, biochemical, or physiologic measurement from or on the organism that is often accepted by governmental agencies (e.g., FDA) or medical opinion to be a sufficient therapeutic target in its own right, independent of "hard" clinical outcomes such as mortality, lost work days, morbidity, etc. There are relatively few accepted surrogate biomarkers in the U.S. and these include blood pressure and blood glucose levels. Such surrogate biomarkers are not the subject of the methods described herein.

By "evaluate" or "evaluation" or "evaluating," in the context of the present methods described herein, is meant a process whereby the activity, toxicity, relative potency, potential therapeutic value and/or efficacy, significance, or worth of a chemical entity, biological factor, combination of chemical entities, or combination of biological factors is determined through appraisal and study, usually by means of comparing experimental outcomes to established standards and/or conditions. The term embraces the concept of providing sufficient information for a decision-maker to make a "go/no go" decision on a chemical entity or biological factor (or combinations of chemical entities or combinations of biological factors) to proceed further in the drug development process. A "go/no go" decision may be made at any point or milestone in the drug development process including, but not limited to, any stage within pre-clinical development, the pre-clinical to Investigational New Drug (IND) stage, the Phase I to Phase II stage, the Phase II to more advanced phases within Phase II (such as Phase IIb), the Phase II to Phase III stage, the Phase III to the New Drug Application (NDA) or Biologics License Application (BLA) stage, or stages beyond (such as Phase IV or other post-NDA or post-BLA stages). The term also embraces the concept of providing sufficient information to select "best-in-breed" (or "best-of-breed") in a class of compounds (chemical entities, biologics).

By "characterize," "characterizing," or "characterization," in the context of the present methods described herein is meant an effort to describe the character or quality of a chemical entity or combination of chemical entities. As used herein, the term is nearly equivalent to "evaluate," yet lacks the more refined aspects of "evaluate," in which to "evaluate" a drug includes the ability to make a "go/no go" decision (based on an assessment of therapeutic value) on proceeding with that drug or chemical entity through the drug development process.

By "condition" or "medical condition" is meant the physical status of the body as a whole or of one of its parts. The term is usually used to indicate a change from a previous physical or mental status, or an abnormality not recognized by medical authorities as a disease or disorder. Examples of "conditions" or "medical conditions" include obesity and pregnancy.

By "candidate therapy" is meant any process by which a disease may be treated that can be screened for effectiveness as outlined herein. Candidate therapies may include behavioral, exercise, or dietary regimens. Candidate therapies may also include treatments with a medical device, or the implantation of a medical device. Candidate therapies may also include therapy with any "candidate agent" or "candidate drug" (see infra).

Candidate therapies may include combinations of candidate therapies. Such a combination may be two different candidate agents. A combination may also be a candidate agent and a dietary regimen. A combination may also be an exercise regimen and a dietary regimen. A combination may also be an exercise regimen and a dietary regimen and a candidate agent. A combination may also be a combination of candidate agents or a combination of candidate agents coupled with another candidate therapy such as exercise or a dietary regimen or both. A combination is therefore more than one candidate therapy administered to the same subject.

Candidate therapies may already be approved for use in humans by an appropriate regulatory agency (e.g., the US Food and Drug Administration or a foreign equivalent). Candidate therapies may already be approved for use in humans for the treatment or prevention of atherogenesis, arteriosclerosis, atherosclerosis, or other cholesterol-related diseases.

By "candidate agent" or "candidate drug" is meant any compound, molecule, polymer, macromolecule or molecular complex (e.g., proteins including biotherapeutics such as antibodies and enzymes, small organic molecules including known drugs and drug candidates, other types of small molecules, polysaccharides, fatty acids, vaccines, nucleic acids, etc) that can be screened for activity as outlined herein. Candidate agents are evaluated in the present methods described herein for discovering potential therapeutic agents that affect cholesterol metabolism and transport.

Candidate agents encompass numerous chemical classes. In one embodiment, the candidate agent is an organic molecule, preferably small organic compounds having a molecular weight of more than 100 and less than about 2,500 daltons. Particularly preferred are small organic compounds having a molecular weight of more than 100 and less than about 2,000 daltons, more preferably less than about 1500 daltons, more preferably less than about 1000 daltons, and still more preferably less than 500 daltons. Candidate agents comprise functional groups necessary for structural interaction with proteins or other host molecules, particularly hydrogen bonding, and typically include at least one of an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof Candidate agents include "known drugs" or "known drug agents" or "already-approved drugs", terms which refer to agents that have been approved for therapeutic use as drugs in human beings or animals in the United States or other jurisdictions. Known drugs also include, but are not limited to, any chemical compound or composition disclosed in, for example, the 13th Edition of *The Merck Index* (a U.S. publication, Whitehouse Station, N.J., USA), incorporated herein by reference in its entirety.

Candidate agents are obtained from a wide variety of sources including libraries of synthetic or natural compounds. For example, numerous means are available that are well known in the art for random and directed synthesis of a wide variety of organic compounds and biomolecules, including expression and/or synthesis of randomized oligonucleotides and peptides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs and thereby rendering them distinct candidate agents.

The candidate agents may be proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the methods described herein. "Amino acid" also includes imino acid residues such as proline and hydroxyproline. The side chains may be in either the (R) or the (S) configuration. If non-naturally occurring side chains are used, non-amino acid substituents may be used, for example to prevent or retard in vivo degradations. Peptide inhibitors of enzymes find particular use.

The candidate agents may be naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian proteins, with the latter being preferred, and human proteins being especially preferred.

The candidate agents may be antibodies, a class of proteins. The term "antibody" includes full-length as well antibody fragments, as are known in the art, including Fab, Fab2, single chain antibodies (Fv for example), chimeric antibodies, humanized and human antibodies, etc., either produced by the modification of whole antibodies or those synthesized de novo using recombinant DNA technologies, and derivatives thereof.

The candidate agents may be nucleic acids. By "nucleic acid" or "oligonucleotide" or grammatical equivalents herein means at least two nucleotides covalently linked together. A nucleic acid of the present methods described herein will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644, 048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowski, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook, and peptide nucleic acids. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine, hypoxathanine, isocytosine, isoguanine, 4-acetylcytosine, 8-hydroxy-N6-methyladenosine, aziridinylcytosine, pseudoisocytosine, 5-(carboxyhydroxlmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, etc.

As described above generally for proteins, nucleic acid candidate agents may be naturally occurring nucleic acids, random and/or synthetic nucleic acids. For example, digests of prokaryotic or eukaryotic genomes may be used as is outlined above for proteins. In addition, RNA interference sequences (RNAi's) are included herein.

Additionally, candidate agents may include chemical entities, drug leads, known drugs, biological factors, or compounds, all of which are defined, infra.

"Chemical entity" includes any chemical, whether new or known, that is administered to a living system for the purpose of screening it for biological or biochemical activity toward the goal of discovering potential therapeutic agents (drugs or drug candidates or drug leads) or uncovering toxic effects (industrial chemicals, pesticides, herbicides, food additives, cosmetics, and the like).

"Drug leads" or "drug candidates" are herein defined as chemical entities or biological molecules that are being evaluated as potential therapeutic agents (drugs). "Drug agents" or "agents" are used interchangeably herein and describe any composition of matter (e.g., chemical entity or biological factor) that is administered, approved or under testing as potential therapeutic agent or is a known therapeutic agent.

"Known drugs" or "known drug agents" or "already-approved drugs" refers to compounds (i.e., chemical entities or biological factors) that have been approved for therapeutic use as drugs in human beings or animals in the United States or other jurisdictions. In the context of the present methods described herein, the term "already-approved drug" means a drug having approval for an indication distinct from an indication being tested for by use of the methods disclosed herein. Using psoriasis and fluoxetine as an example, the methods described herein allow one to test fluoxetine, a drug approved by the FDA (and other jurisdictions) for the treatment of depression, for effects on biomarkers of psoriasis (e.g., keratinocyte proliferation or keratin synthesis); treating psoriasis with fluoxetine is an indication not approved by FDA or other jurisdictions. In this manner, one can find new uses (in this example, anti-psoriatic effects) for an already-approved drug (in this example, fluoxetine).

"Biological factor" refers to a compound or compounds made by living organisms having biological or physiological activities (e.g., preventive, therapeutic and/or toxic effects). Examples of biological factors include, but are not limited to, vaccines, polyclonal or monoclonal antibodies, recombinant proteins, isolated proteins, soluble receptors, gene therapy products, environmental toxins, and the like. As used herein, the term "biologics" is synonymous with "biological factor."

"Compound" means, in the context of the present disclosure, any new chemical entity, chemical entity, drug lead, drug candidate, drug, drug agent, agent, known drug, known drug agent, already-approved drug, biologic, or biological factor, food additives, industrial chemicals, environmental pollutants and the like. The term is meant to encompass all chemical and biological molecules.

By "subject" is meant the living subject of the experiment or procedure or process being described. All subjects are living systems. In one embodiment, a subject may be a human. In another embodiment, a subject may be a rabbit or a rodent or a non-human primate. Additionally, the term "subject" encompasses any other living system.

By "living system" is meant herein any living entity including a cell, cell line, tissue, organ or organism. Examples of organisms include any animal, preferably a vertebrate, more preferably a mammal, most preferably a human. Examples of mammals include nonhuman primates, farm animals, pet animals(e.g., cats and dogs), and research animals (e.g., mice, rats, and humans).

A "biological sample" encompasses any sample obtained from a living system or subject. The definition encompasses blood, tissue, and other samples of biological origin that can be collected from a living system or subject. Preferably, biological samples are obtained through sampling by minimally invasive or non-invasive approaches (e.g., urine collection, stool collection, blood drawing, needle aspiration, and other procedures involving minimal risk, discomfort or effort). Biological samples can be gaseous (e.g., exhaled breath). Biological samples are often liquid (sometimes referred to as a "biological fluid"). Liquid biological samples include, but are not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, and others. Biological samples include samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

Methods

The methods described herein are useful for determining pancreatic β-cell sufficiency. Pancreatic β-cell sufficiency is indicative of the capacity of a subject to compensate for insulin resistance. Further, the methods are also useful for determining the level of insulin resistance. Insulin resistance indicates reduced sensitivity of tissues to the actions of insulin. Taken in conjunction, pancreatic β-cell sufficiency and insulin resistance are highly predictive of susceptibility to developing type 2 diabetes mellitus or likelihood of progressing to a more advanced DM2. Determination of pancreatic β-cell sufficiency and/or insulin resistance may also have numerous other uses, as described herein.

A. Administering Isotope-Labeled Precursor(s)

1. Compositions Including Sugars (Sugar Compositions)

Compositions including sugars may include monosaccharides, polysaccharides, or other compounds attached to monosaccharides or polysaccharides. Isotope-labeled sugar compositions may be administered to a subject as monosaccharides or as polymers including monosaccharide residues. Isotope labeled sugar compositions may be labeled with $^2H$, $^3H$, $^{18}O$, $^4C$, $^{13}C$, or other isotopes. Isotope-labeled sugar compositions may be administered to a subject as monosaccharides or as polymers composed of monosaccharide residues. Isotope-labeled monosaccharides may be readily obtained commercially (for example, Cambridge Isotopes, Massachusetts). Relatively low quantities of isotope-labeled sugar composition need to be administered. Quantities may be on the order of milligrams, $10^1$ mg, $10^2$ mg, $10^3$ mg, $10^4$ mg, $10^5$ mg, or $10^6$ mg. Isotope-labeled sugar enrichment may be maintained for weeks or months in humans and in animals without any evidence of toxicity. The lower expense of commercially available isotope-labeled monosaccharides, and low quantity that need to be administered, allow maintenance of enrichments at low expense.

In one particular variation, the isotope-labeled sugar composition is $^2H$-glucose. FIG. 6 shows the fate of $^2H$-labeled glucose. Glucose is metabolized by glycolysis and the citric acid cycle. Glycolysis releases most of the H-atoms from C—H bonds of glucose; oxidation via the citric acid cycle ensures that all H-atoms are released to $H_2O$. The loss of $^3H$- or $^2H$-label by glucose has been used to assess glycolysis, an intracellular metabolic pathway for glucose (Katz, J., and R. Rognstad. Futile cycles in the metabolism of glucose. In: Current Topics in Cellular Regulation. Vol 10, edited by B. Horecker and E. Stadman. New York: Academic Press, 1976, p. 238-239.). Some investigators have used release of $^3H$ from intravenously administered $^3H$-glucose into $^3H_2O$ as a measure of glycolysis (Rossetti L, Lee Y T, Ruiz J, Aldridge S C, Shamoon H, Boden G. Quantitation of glycolysis and skeletal muscle glycogen synthesis in humans. Am J Physiol 265: E761-9, 1993.). Prior to the present disclosure, release of $^2H$-glucose into $^2H_2O$ had not been used previously, because of the expectation that the body water pool is too large relative to $^2H$ administration in labeled glucose to achieve measurable $^2H_2O$ levels. In a further variation, the labeled glucose may be [6,6-$^2H_2$]glucose, [1-$^2H_1$]glucose, and [1,2,3,4,5,6-$^2H_7$]glucose.

In another variation, the isotope-labeled sugar composition may include fructose or galactose. Fructose enters glycolysis via the fructose 1-phosphate pathway, and secondarily through phosphorylation to fructose 6-phosphate by hexokinase. Galactose enters glycolysis via the galactose to glucose interconversion pathway.

Other monosaccharides which find use, include, but are not limited to, trioses, pentoses, hexoses, and higher order monosaccharides. Monosaccharides further include, but are not limited to, aldoses and ketoses.

In another variation, the isotope-labeled sugar composition may include polymers. The polymers may include polysaccharides. For example, labeled glycogen, a polysaccharide, includes glucose residues. In another variation, labeled polysaccharides may be introduced. As further variation, labeled sugar monomers may be administered as a component of sucrose (glucose α-(1,2)-fructose), lactose (galactose β-(1,4)-glucose), maltose (glucose α-(1,4)-glucose), starch (glucose polymer), or other polymers.

In one variation, the sugar composition is a mixture of isotope-labeled and unlabeled sugar compositions.

In one variation, the isotope-labeled sugar composition is 15 grams of $6,6,-^2H_2$-glucose mixed with 35 grams of unlabeled glucose, dissolved in an aqueous solution, and administered orally to a human subject. In another variation, the sugar composition is 15 grams of $6,6,-^2H_2$-glucose mixed with 60 grams of unlabeled glucose, dissolved in an aqueous solution, and administered orally to a human subject. In another variation, the aqueous solution is flavored or colored or both.

In one variation, the isotope-labeled sugar composition is $6,6,-^2H_2$-glucose which is administered to animal subjects by oral gavage and the amount administered is determined based on the weight of the subject.

In one variation, the labeled sugar may be administered orally, by gavage, intraperitoneally, intravenously, subcutaneously, or other bodily routes. In another variation, the sugars may be administered to a subject orally, optionally as part of a food or drink. In other variations, the sugars are administered by other routes.

In one variation, the subject may be a mammal. In another variation, the subject may be a rodent, primate, hamster, guinea pig, dog, or pig. The subject may be an experimental animal. In another variation, the subject may be a human.

B. Obtaining One or More Biological Samples from a Subject

A biological sample, (e.g., as defined, supra), is obtained from a subject. Specific methods of obtaining biological samples are well known in the art. In one variation, water may be partially purified from the sample. In another variation, the water may be isolated from the sample.

In one variation, the one or more biological samples may be obtained after a period of time. In another variation, the one or more biological samples may be obtained multiple times. One or more biological samples may be obtained prior to the administration of the labeled sugar composition.

C. Measuring the Isotopic Contents of Sugar Metabolites

In certain embodiments, the detection of isotope-label into sugar metabolites may be performed in vivo. In other embodiments, the detection is performed in vitro.

Any sugar metabolite may find use in the methods described herein. In one embodiment, the sugar metabolite is water. In other embodiments, the sugar metabolite may be lactate, pyruvate or NADH.

1. Mass Spectrometry

The isotope label, or alternatively, the labeled chemical compositions, may be determined by various methods such as mass spectrometry, particularly gas chromatography-mass spectrometry (GC-MS). Incorporation of labeled isotopes into chemical compositions may be measured directly. Alternatively, incorporation of labeled isotopes may be determined by measuring the incorporation of labeled isotopes into one or more hydrolysis or degradation products of the chemical composition. The hydrolysis or degradation products may optionally be measured following either partial purification or isolation by any known separation method, as described previously.

Mass spectrometers convert components of a sample into rapidly moving gaseous ions and separate them on the basis of their mass-to-charge ratios. The distributions of isotopes or isotopologues of ions, or ion fragments, may thus be used to measure the isotopic enrichment in one or more chemical compositions, or chemical or biochemical degradation products.

Generally, mass spectrometers comprise an ionization means and a mass analyzer. A number of different types of mass analyzers are known in the art. These include, but are not limited to, magnetic sector analyzers, electrostatic analyzers, quadrupoles, ion traps, time of flight mass analyzers, and fourier transform analyzers. In addition, two or more mass analyzers may be coupled (MS/MS) first to separate precursor ions, then to separate and measure gas phase fragment ions.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

Many types of mass spectrometer can be used to make the measurements required by the present methods described herein. It may be an isotope ratio mass spectrometer, which may be coupled with a pyrolysis unit, combustion unit, GC unit, or combinations thereof. It may be cycloidal mass spectrometer. It may be any of the types of mass spectrometer discussed above or known in the art. The measurements may be made directly on the biological samples, or it may be further processed before analysis. Processing may include covalent modification of the water, or abstraction of hydrogens or deuteriums from the water, or other types of chemical modification. The processing may occur on whole biological samples, fractions of biological samples, or purified components of biological samples.

In general, the measurements contemplated herein can be carried out with a broad range of instrument types operating in a broad range of modes, on a broad range of sample types processed different amounts. The above list is non-limiting.

In addition, where the isotope is radioactive, isotopic content or isotopic. pattern or abundances may be measured using techniques known in the art for the measurement of radioisotopes, including, but not limited to, liquid scintillation counting, geiger counting, CCD based detection, film based detection, and others.

The actual isotopic content or isotopic pattern may be calculated from data obtained as described, supra. These calculations can take many forms, depending on the amount of historical or baseline data available, the preference of the practitioner, the desired accuracy or precision of the measurements, the type of instrument used for the analysis, and other factors. Example calculations follow:

2. Measuring Relative and Absolute Mass Isotopomer Abundances

Mass spectrometers measure the relative quantity of different mass molecules or atoms in a sample. These quantities are sometimes referred to as abundances. Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the methods described herein. In one embodiment, the relative abundances of different mass isotopomers are measured by GC/MS and the molar percent excess of given isotopomer is calculated. In another embodiment, the relative abundances of different isotopes are measured at the atomic level by GC-combustion isotope ratio-mass spectrometry (GCC-IRMS), or GC-pyrrolysis-isotope ratio-mass spectrometry (GCP-IRMS), and the atom percent excess of a given isotopomer is calculated.

a. Calculating Isotopic Content or Isotopic Pattern

I. Molar Percent Excess (MPE)

Isotopic content or isotopic pattern may be calculated from abundance data collected as described, supra. In one embodiment, isotopic content or isotopic pattern is expressed as molar percent excess (MPE). To determine MPE, the practitioner first determines the fractional abundance of an isotopomer of the molecule of interest (usually, the molecule of interest is the stable-isotope labeled metabolite of the stable-isotope labeled sugar). This can be calculated from abundance data, such as that from GC/MS, using the following equation, which is a general form for the determination of fractional abundance of a mass isotopomer $M_x$:

$$\text{Fractional abundance of } M_x = \frac{AbundanceM_x}{\sum_{i=0}^{n} AbundanceM_i},$$

where 0 to n is the range of nominal masses relative to the lowest mass ($M_0$) mass isotopomer in which abundances occur.

Once the fractional abundance is determined, it is compared to the baseline, historical baseline, theoretical baseline, or other such reference values (obtained as described, supra) in order to determine the MPE. This is calculated using the following equation:

$$MPE = EM_X$$
$$= \Delta \text{ fractional abundance}$$
$$= \text{enrichment}$$
$$= (M_X)_e - (M_X)_b$$
$$= \left(\frac{AbundanceM_X}{\sum_{i=0}^{n} AbundanceM_i}\right)_e - \left(\frac{AbundanceM_X}{\sum_{i=0}^{n} AbundanceM_i}\right)_b,$$

where subscript e refers to enriched and b refers to baseline or natural abundance.

Once the MPE is determined, the fraction of molecules derived from the stable isotope-labeled sugar or the extent of dilution by endogenous molecules can be determined. In both cases, the MPE is compared to a value representing the maximum possible molar percent excess. In the case where a molecule of interest is produced by the metabolism of the isotope-labeled sugar (e.g., the production of $^2H_2O$ from $^2H_2$-glucose), the MPE of the precursor may be measured and used directly or as a basis for calculation of a maximum potential MPE. The maximum potential MPE may also be determined from historical data, from calculations based on the amount of isotope-labeled sugar administered, from similar calculations that take into account properties of the subject (e.g., weight, body composition), from purely theoretical calculations, and from other combinations of estimation, measurement, and retrospective data analysis. The maximum possible MPE may also be determined by measuring the MPE in a separate biological sample that is known to contain fully labeled molecule of interest. In the case of dilution of label, the maximum possible MPE is based on the MPE of the administered isotope-labeled sugar composition.

The Applicant has considerable experience in the field of isotope label incorporation and isotopomer distribution, and has developed a number of technologies and modes of calculation relevant to the calculation and analysis of isotopic content or isotopic pattern. These include the Mass Isotopomer Distribution Analysis (MIDA), and are described extensively, particularly in U.S. Pat. Nos. 5,338,686, 5,910, 403, and 6,010,846, which are hereby incorporated by reference in their entirety. Variations of MIDA and other relevant techniques are further described in a number of different sources known to one skilled in the art, including Hellerstein and Neese (1999), as well as Chinkes, et al. (1996), and Kelleher and Masterson (1992), U.S. patent application Ser. Nos. 10/279,399, and 10/701,990, all of which are hereby incorporated by reference in their entirety.

In addition to the above-cited references, calculation software implementing the method is publicly available from Professor Marc Hellerstein, University of California, Berkeley.

II. Atom Percent Excess (APE)

Isotopic content or isotopic pattern may be calculated from abundance data collected as described, supra. In one embodiment, isotopic content or isotopic pattern is expressed as atom percent excess (APE). To determine APE, the practitioner first determines the fractional abundance of the isotope of interest in the molecule of interest (usually, the molecule of interest is the stable-isotope labeled metabolite of the stable-isotope labeled sugar). This can be calculated from abundance data, such as that from GCC-IRMS or GCP-IRMS using the following equation, which is a general form for the determination of fractional abundance of a isotope $I_X$:

$$\text{Fractional abundance of } I_X = A_X = \frac{AbundanceI_X}{\sum_{i=0}^{n} AbundanceI_i}$$

where 0 to n is the range of possible isotopes of the chosen atom in which abundances are measured.

Once the fractional abundance is determined, it is compared to the baseline, historical baseline, theoretical baseline, or other such reference values (obtained as described, supra)

in order to determine the atom percent excess (APE). This is calculated using the following equation:

$$APE = \Delta \text{ fractional abundance}$$
$$= \text{enrichment}$$
$$= (A_X)_e - (A_X)_b$$
$$= \left(\frac{Abundance_X}{\sum_{i=0}^{n} Abundance_i}\right)_e - \left(\frac{Abundance_X}{\sum_{i=0}^{n} Abundance_i}\right)_b,$$

where subscript e refers to enriched and b refers to baseline or natural abundance.

Once the APE is determined, the fraction of molecules derived from the stable isotope-labeled sugar or the extent of dilution by endogenous molecules can be determined. This is carried out as described, supra, but may require additional calculations in the case of the theoretical maximum APE. Such calculations are known to those with skill in the art.

III. Atom Percent Excess (APE)

In the present methods described, isotopic content or isotopic pattern is often expressed as MPE or as an APE. Molar percent excess is sometimes written as $EM_x$, and refers to the molar percent excess of a given mass (with respect to all possible masses of the molecule being analyzed as compared to the baseline sample, historical baseline data, or predicted baseline values). Many combinations of administered isotope-labeled sugars or sugar compositions and isotope-labeled metabolites are contemplated.

3. Metabolism

Very low quantities of isotope-labeled metabolite may be detected. The isotope-labeled metabolite may be water. In one embodiment, 1 part in $10^3$ isotope-labeled metabolite may be identified. In another embodiment, 1 part in $10^4$ isotope-labeled metabolite may be identified. In another embodiment, 1 part in $10^5$ isotope-labeled metabolite may be identified. In another embodiment, 1 part in $10^6$ isotope-labeled metabolite may be identified. In another embodiment, 1 part in $10^7$ isotope-labeled metabolite may be identified.

4. Detecting Isotope-labeled Metabolite Following Sugar Metabolism

The methods of measuring the consequences of sugar ingestion may be accomplished by measuring sugar metabolism products. The rate of isotope-labeled metabolite production from the oxidation of fuels, including sugars, is sufficient to achieve relatively high levels of isotope-labeled metabolite when modest doses of compounds containing isotope-labeled sugars are administered.

Alternatively, isotope-labeled sugars may be polymerized to form labeled glycogen, which may then be measured.

Isotope-labeled water or isotope-labeled metabolite production may be corrected for a baseline value.

D. Measuring Insulin Concentrations in Biological Samples

A number of techniques for measuring the concentration of insulin in a biological sample are available. For instance, an enzyme linked immunosorbent assay (ELISA) or radioimmunoassay (RIA) kit can be purchased (many manufacturers of such kits exist, e.g., Crystal Chem, Inc, Downer's Grove, Ill.) and used, according to the manufacturers instructions, to measure the concentration of insulin in a biological sample. Alternatively, samples may be sent for analysis by a commercial laboratory that performs such analyses on a fee for service basis (e.g., Linco Research, St Charles, Mo.).

E. Calculating Insulin AUC (INS AUC) and Calculating Dimensions of Pathogenesis

After the incorporation of isotope label from the administered sugar composition into sugar metabolites has been determined and the insulin levels have been determined, the data can be analyzed in order to calculate the two parameters relevant to DM2, namely the sufficiency of the pancreatic response (moles labeled metabolite produced, or moles glucose utilized, e.g., moles $^2H_2O$ produced) and the level of insulin resistance in tissues (moles labeled metabolite produced or moles sugar utilized divided by the INS AUC, e.g., moles $^2H_2O$/INS AUC).

1. Calculating the Amount of Isotope-labeled Metabolite Produced

The amount of isotope-labeled metabolite produced is determined by determining the total body water of the subject, and then multiplying the observed concentration of isotope-labeled metabolite times the volume of the subject's total pool within which that metabolite is diluted. In embodiments utilizing a isotope labeled metabolite other than isotope-labeled water (e.g. lactate, pyruvate, NADH, etc.), the total body pool of the utilized metabolite is determined.

If the isotope-labeled metabolite is water, the total body water is determined. This is done using techniques known in the art, and may include determining the lean body mass of the subject (e.g., by bioelectrical impedance testing) and then applying normal equations to determine the total amount of water in the subject. Alternatively, a known amount of $H_2^{18}O$ can be administered to the subject concurrently with or at some time before or after the administration of the isotope-labeled sugar composition, and, after a period of time, a biological sample is taken (the sample may be a sample collected for an insulin or isotope-labeled metabolite measurement, or it may be a different sample). The $^{18}O$ APE in the sample is then determined as described, supra, and the size of the total body water pool is then determined by the dilution method, described in more detail infra.

In one embodiment, a blood sample taken from a human subject three hours after administration of a $^2H$-labeled sugar composition has a fractional blood $^2H_2O$ level of 0.000026 (i.e., 0.0026% of the water in the body is $^2H_2O$—the APE of $^2H$ is 0.0026%). This subject is found by biological impedance to have a total body water pool of 45 liters. The percent $^2H_2O$ is multiplied times the total volume to give mls of $^2H_2O$:

$$\left(.000026\left(\frac{ml^2\ H_2O}{ml\ H_2O}\right)\right) \times (45,000\ ml\ H_2O/subject) = 1.17\frac{ml^2\ H_2O}{subject}$$

The density of water is taken as 1, so 1.17 mls of $^2H_2O$ means that 1.17 grams of $^2H_2O$ were produced. The mass of $^2H_2O$ is divided by the molecular weight of $^2H_2O$ (20 grams/mole) in order to get the moles $^2H_2O$ produced:

1.17 grams/(20 grams/mole)=0.0585 moles=58.5 millimoles

The amount of isotope-labeled metabolite produced (e.g. moles $^2H_2O$) provides the pancreatic β-cell sufficiency which is indicative of the sufficiency of insulin secretion. However, the amount of isotope-labeled metabolite produced alone cannot fully resolve whether the subject is in the healthy, normal range or if the subject is exibiting compensated insulin resistance. FIG. 3. For a more detailed determination of the subject's susceptibility to developing DM2 or for progressing to a more advanced form of DM2, a determination of the the subject's insulin resistance value is especially useful.

The amount of isotope-labeled metabolite produced may also be used in conjunction with a measure of insulin production to determine the insulin resistance value, as described supra.

2. Calculating Insulin AUC

The insulin area under curve (INS AUC or AUC) reflects the total exposure of tissues to insulin over the period of study. It is calculated using techniques known in the art, (e.g., by the "trapezoid" method), using insulin levels determined in biological samples taken at various times after the administration of the sugar composition. A baseline value may also be determined from a sample taken before the administration of the sugar composition. Only one time point after the administration of the sugar composition may be used, or many may be used. At least two values determined taken at different time points should be used to determine insulin AUC. The insulin AUC is expressed with units of:

(concentration)×(time)

for instance:

(picoMoles/liter)×(hours)

Discussion of this and other AUC techniques can be found in, for instance, *Applied Biopharmaceutics and Pharmacokinetics*, L. Shargel and A. Yu, authors, 4$^{th}$ edition, McGraw Hill, Medical Publishing Division, which is hereby incorporated by reference in its entirety for the purpose of describing AUC techniques.

Alternatively, other measures of insulin production may be used to evaluate the insulin levels in the subject. For example, the maximum concentration of insulin may be measured, or the concentration of insulin at a given time in a given type of biological sample may be measured. In one embodiment, insulin production is measured through c-peptide die-away curves. In general, the AUC will be calculated for a given subject, but single time point concentrations or other insulin measures may be used in place of the AUC.

3. Evaluating Dimensions of Diabetes Pathogenesis

Two dimensions of diabetes pathogenesis, as discussed, supra, are evaluated for each subject. In one embodiment, the first dimension, which is insulin sensitivity or resistance, is represented by the moles of isotope-labeled sugar metabolite produced or absolute moles of sugar metabolite produced divided by the INS AUC (e.g., moles $^2H_2O$ produced divided by INS AUC). The units of the isotope-labeled metabolite/ AUC insulin parameter may be omitted for clarity (e.g., this parameter may be considered "unitless"), or included. In alternate embodiments, insulin sensitivity or resistance is represented by the moles of isotope-labeled sugar metabolite produced or absolute moles of sugar metabolite produced divided by a non-INS AUC measure of insulin production. The second dimension, which is pancreatic beta-cell response, is represented by the absolute moles of labeled metabolite produced (e.g. absolute moles of $^2H_2O$ produced) or absolute moles of sugar utilized. For each subject, these parameters are determined, and the subject is then compared to other subjects, reference values, historical data from similar subjects, or data from a previous measurement on the same subject. If the measurements are made in the context of drug development, the observed dimensions of pathogenesis may be compared to treated or untreated groups, or to measurements from the same subject that were made prior to the initiation of treatment.

The two parameters may be displayed graphically on a chart as shown in FIG. 2.

4. EGP Correction

If desired, corrections for endogenous glucose production (EGP) can be made by the dilution method. In some patients, EGP (e.g., hepatic production of glucose from glycogen stores) may contribute to the total glucose load, and can dilute the isotope-labeled sugar composition in vivo, thereby skewing results of the above measurements. In such a scenario, a biological sample (e.g., blood) can be analyzed by mass spectrometry for the amount of stable-isotope labeled sugar present. For example, if a human subject is given a 75 gram dose of glucose, of which 15 grams is 6,6-$^2H_2$-glucose, then the mole percent excess of $^2H_2$-glucose (the $EM_2$) in blood would be 20% if no EGP had occurred. If, for instance, the mole percent excess of $^2H_2$-glucose was seen to be only 15%, then this means that 25 grams of glucose were produced endogenously. For a detailed discussion of these calculations see Robert R. Wolfe, Radioactive and Stable Isotope Tracers in Biomedicine (Wiley-Liss 1992).

F. Techniques and Compositions

One or more chemical compositions may be obtained, and optionally partially purified or isolated, from the biological sample using standard biochemical methods known in the art. Chemical compositions include, but are not limited to, glucose, glycogen, or any other mono or polysaccharide as described above. Optionally, fragments of the compositions may also be obtained. The frequency of biological sampling can vary depending on different factors. Such factors include, but are not limited to, the nature of the chemical composition tested, ease of sampling, and half-life of a drug used in a treatment if one is monitoring responses to the treatment.

In one variation, the one or more chemical compositions may be glucose. In a further variation, the dilution of orally administered labeled sugars (e.g., $^2H$-glucose) in plasma glucose load reveals endogenous glucose production (EGP, FIG. 6) Considerable information can be gained about glucose utilization and synthesis pathways in the body by use of this approach. FIG. 6 depicts the glucose metabolism pathway, including deuterium-labeled glucose. Glucose ingested by a subject is delivered to tissues, optionally stored as glycogen, or converted to water and carbon dioxide via glycolysis and the citric acid cycle. Labeled water, particularly $^2H_2O$, may then be returned to the blood stream, and incorporated into bodily fluids, then into biosynthetic products. In a still further variation, the proportion of glucose may be used to identify the proportion of administered $^2H$-labeled glucose undergoing glycolysis.

In another variation, the one or more chemical compositions may be glycogen.

Uses of the Present Methods

The methods disclosed herein allow for diagnostic classification of patients for decisions regarding therapeutic interventions (e.g., insulin-sensitizing and pancreatic beta-cell-stimulating agents); clinical differentiation between type I DM and type 2 DM (DM2); clinical monitoring of treatments intended to reduce risk of developing DM2 in non-diabetic subjects (e.g., insulin-sensitizing and pancreatic beta-cell-stimulating agents); clinical monitoring of agents intended to improve existing DM2 and prevent progression of DM2 (e.g., insulin-sensitizing and pancreatic beta-cell-stimulating agents); clinical development and testing of new compounds and candidate agents to prevent progression to DM2 or disease progression in existing DM2 (e.g., insulin-sensitizing and pancreatic beta-cell-stimulating agents); clinical use as an end-point biomarker in FDA Phase II-IV clinical trials of drugs intended to prevent progression to DM or disease progression in existing DM2 (e.g., insulin-sensitizing and pancreatic beta-cell-stimulating agents); identifying genes associated with insulin resistance, pancreatic response, and susceptibility to DM2.

The methods disclosed herein also allow for a reliable measure of tissue insulin resistance in an experimental animal concurrently with a reliable measure of the adequacy of pancreatic beta-cell response in an experimental animal.

The methods disclosed herein also allow for characterization of animal models for utility in diabetes research; testing of new compounds or candidate agents in pre-clinical models of DM (e.g., insulin-sensitizing and pancreatic beta-cell-stimulating agents); comparison of potency, route of administration, congeners in a class, etc. for selection of candidate agents for therapy of DM (e.g., insulin-sensitizing and pancreatic beta-cell-stimulating agents); and identification of genes associated with insulin resistance, pancreatic response and susceptibility to DM2.

Kits

Also provided are kits for determining tissue insulin resistance and the sufficiency of pancreatic beta-cell response. The kits may include isotope-labeled precursor molecules, and may additionally include chemical compounds known in the art for separating, purifying, or isolating proteins, and/or chemicals necessary to obtain a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for obtaining samples from the cell, tissue, or organism (e.g., specimen cups, needles, syringes, and tissue sampling devices) may also be optionally provided.

Information Storage Devices

Also provided are information storage devices such as paper reports or data storage devices including data collected from the methods described herein. An information storage device includes, but is not limited to, written reports on paper or similar tangible medium, written reports on plastic transparency sheets or microfiche, and data stored on optical or magnetic media (e.g., compact discs, digital video discs, optical discs, magnetic discs, and the like), or computers storing the information whether temporarily or permanently. The data may be at least partially contained within a computer and may be in the form of an electronic mail message or attached to an electronic mail message as a separate electronic file. The data within the information storage devices may be "raw" (i.e., collected but unanalyzed), partially analyzed, or completely analyzed. Data analysis may be by way of computer or some other automated device or may be done manually. The information storage device may be used to download the data onto a separate data storage system (e.g., computer, hand-held computer, and the like) for further analysis or for display or both. Alternatively, the data within the information storage device may be printed onto paper, plastic transparency sheets, or other similar tangible medium for further analysis or for display or both.

EXAMPLES

The following non-limiting examples further illustrate the methods disclosed herein:

Example 1

Monitoring of a Human Subject

A human subject may be tested by the methods disclosed herein. A subject, who had fasted overnight, enters the clinic and has blood drawn (0 hour timepoint), and then receives a solution containing 75 grams of glucose. 15 of the 75 grams of glucose would be $6,6^2H_2$-glucose. The subject drinks the glucose solution. The subject then has additional blood drawn at 1, 2, 3, and 4 hours after drinking the solution (1, 2, 3, and 4 hour timepoints).

Portions of the blood from all five timepoints are sent out for insulin measurement, as described, supra. The insulin AUC is determined as described, supra.

A portion of the blood from the four hour timepoint is processed for $^2H_2O$ analysis. Specifically, 100 ul of the blood is transferred to the inverted cap of a 2 ml polypropylene screw cap vial, the vial is screwed onto the cap, and the inverted vial is placed in a 70 degree Celsius glass bead filled heating block overnight. The condensed vapor at the top of the inverted vial is then collected by centrifugation, and analyzed on an isotope-ratio mass spectrometer equipped with a pyrolysis unit (P/IRMS). The $^2H_2O$ APE in the sample is determined by comparing the observed data to a standard curve constructed with samples of known $^2H_2O$ APE. Absolute moles of $^2H_2O$ produced in the four hours post-administration of the sugar composition are calculated as described, supra.

The disease state of the subject is further assessed by plotting the moles $^2H_2O$ produced and the moles of $^2H_2O$ produced divided by the AUC insulin and placing the individual in one of the quadrants on a chart similar to that shown in FIG. 2.

Example 2

Longitudinal Monitoring of Obese, Non-DM Individuals:

An obese non-DM subject was tested by the methods disclosed herein. Absolute heavy water production was 45 mMoles (out of 83 mMoles administered in deuterated glucose). Normal values are >40-50 mMoles (FIG. 7). The Insulin AUC (INS AUC) was 1.8 nM-hours/liter. The $^2H_2O$/INS AUC was 45/1.8=25. Normal values are 50 and above (FIG. 7). The subject plotted on the two-dimensional graph falls into the compensated insulin resistance (upper left) quadrant (FIG. 7). The subject will be tested again one year later. The following scenarios may be observed:

a) $^2H_2O$/INS AUC decreases to 12, while absolute heavy water production remains stable at 45 nMoles (arrow #1, FIG. 7). The interpretation would be that this person has worse insulin resistance but that the pancreas is keeping up and that beta-cell compensation is adequate.

b) $^2H_2O$/INS AUC decreases to 22 while absolute heavy water production falls to 30 mMoles (arrow #2, FIG. 7). The conclusion here is that insulin resistance has progressed slightly but that beta-cell insufficiency (inadequate beta-cell response) is present. This subject has a high risk for developing DM2 and has a serious medical problem. This subject is then placed on a therapeutic agent and repeat testing occurs in six months.

c) $^2H_2O$/INS AUC remains stable after therapy at 25 while absolute heavy water production increases to 55 mMoles (arrow #3, FIG. 7). The conclusion is that the subject's pancreatic function has improved while insulin resistance has not. The action of the drug given to this subject is thereby characterized.

Example 3

Differentiation Between Types 1 and 2 DM

A normal weight 29-year-old subject is diagnosed with diabetes. The question of DM1 vs. DM2 is uncertain. The test disclosed herein is performed. The results show that $^2H_2O$/INS AUC is in the normal range (75), while absolute heavy water production is low (25 mMoles) putting the subject in the lower right quadrant of FIG. 7. The conclusion is that this subject does not have insulin resistance but has primary pancreatic insufficiency, consistent with DM1.

Example 4

Evaluation of Candidate Therapies:

Methods: A group of borderline type 2 diabetic subjects were characterized using the methods disclosed herein, and plotted as shown in FIG. 8. The subjects were then divided into three groups—one group receiving standard insulin sensitizer therapy (group A), another group receiving a candidate therapy consisting of a pancreatic regenerative factor (group B), and the third group receiving both therapies (group C). After 6 months of treatment, the patients were re-evaluated using the methods disclosed herein.

Results (FIG. 8): As expected, group A showed an improvement in insulin sensitivity and a slight improvement in pancreatic response. The experimental therapy proved successful at improving pancreatic function in group B, but only by a moderate amount. The combination therapy in group C, however, exerted synergistic effects, resulting in a dramatic improvement in disease state.

Example 5

Drug Development in Preclinical Animal Models

Zucker fatty diabetic rats were tested by the methods disclosed herein and as described in U.S. patent application Ser. No. 11/064,197, herein incorporated by reference in its entirety. At weeks six of age, $D_2O$/INS AUC was reduced, but absolute heavy water production was near normal. Some animals were given rosiglitazone in their diet for four weeks, others were not. Repeat testing by the methods disclosed herein was performed.

Rosiglitazone treated animals showed the improved insulin sensitivity indicated, while untreated animals showed a reduction in pancreatic compensation as a result of insulin resistance (FIG. 9).

REFERENCES

Ahren B, Pacini G. 2004. Importance of quantifying insulin secretion in relation to insulin sensitivity to accurately assess beta cell function in clinical studies. Eur J Endocrinol 150(2):97-104.

Bergman R N. 1989. Lilly lecture 1989. Toward physiological understanding of glucose tolerance. Minimal-model approach. Diabetes 38(12):1512-27.

Bergman R N, Finegood D T, Ader M. 1985. Assessment of insulin sensitivity in vivo. Endocr Rev 6(1):45-86.

Boden G, Chen X, Iqbal N. 1998. Acute lowering of plasma fatty acids lowers basal insulin secretion in diabetic and non-diabetic subjects. Diabetes 47(10):1609-12.

Buchanan T A. 2001. Pancreatic B-cell defects in gestational diabetes: implications for the pathogenesis and prevention of type 2 diabetes. J Clin Endocrinol Metab 86(3):989-93.

Byrne M M, Sturis J, Sobel R J, Polonsky K S. 1996. Elevated plasma glucose 2 h postchallenge predicts defects in beta-cell function. Am J Physiol 270(4 Pt 1):E572-9.

Cavaghan M K, Ehrmann D A, Polonsky K S. 2000. Interactions between insulin resistance and insulin secretion in the development of glucose intolerance. J Clin Invest 106(3):329-33.

Cruciani-Guglielmacci C, Vincent-Lamon M, Rouch C, Orosco M, Ktorza A, Magnan C. 2005. Early changes in insulin secretion and action induced by high-fat diet are related to a decreased sympathetic tone. Am J Physiol Endocrinol Metab 288(1):E148-54.

Delaunay F, Khan A, Cintra A, Davani B, Ling Z C, Andersson A, Ostenson C G, Gustafsson J, Efendic S, Okret S. 1997. Pancreatic beta cells are important targets for the diabetogenic effects of glucocorticoids. J Clin Invest 100(8):2094-8.

Ehrmann D A, Breda E, Corcoran M C, Cavaghan M K, Imperial J, Toffolo G, Cobelli C, Polonsky KS. 2004. Impaired beta-cell compensation to dexamethasone-induced hyperglycemia in women with polycystic ovary syndrome. Am J Physiol Endocrinol Metab 287(2):E241-6.

Elbein S C, Hasstedt S J, Wegner K, Kahn S E. 1999. Heritability of pancreatic beta-cell function among nondiabetic members of Caucasian familial type 2 diabetic kindreds. J Clin Endocrinol Metab 84(4):1398-403.

Elbein S C, Wegner K, Kahn S E. 2000. Reduced beta-cell compensation to the insulin resistance associated with obesity in members of caucasian familial type 2 diabetic kindreds. Diabetes Care 23(2):221-7.

Fajans S S, Conn J W. 1954. An approach to the prediction of diabetes mellitus by modification of the glucose tolerance test with cortisone. Diabetes 3(4):296-302; discussion, 302-4.

Henriksen J E, Alford F, Ward G M, Beck-Nielsen H. 1997. Risk and mechanism of dexamethasone-induced deterioration of glucose tolerance in non-diabetic first-degree relatives of NIDDM patients. Diabetologia 40(12):1439-48.

Kahn S E. 2003. The relative contributions of insulin resistance and beta-cell dysfunction to the pathophysiology of Type 2 diabetes. Diabetologia 46(1):3-19.

Kahn S E, Prigeon R L, McCulloch D K, Boyko E J, Bergman R N, Schwartz M W, Neifing J L, Ward W K, Beard J C, Palmer J P and others. 1993. Quantification of the relationship between insulin sensitivity and beta-cell function in human subjects. Evidence for a hyperbolic function. Diabetes 42(11):1663-72.

Kalhan S C, Adam P A. 1975. Inhibitory effect of prednisone on insulin secretion in man: model for duplication of blood glucose concentration. J Clin Endocrinol Metab 41(3):600-10.

Kulkarni R N, Jhala U S, Winnay J N, Krajewski S, Montminy M, Kahn C R. 2004. PDX-1 haploinsufficiency limits the compensatory islet hyperplasia that occurs in response to insulin resistance. J Clin Invest 114(6):828-36.

Pacini G, Bergman R N. 1986. MINMOD: a computer program to calculate insulin sensitivity and pancreatic responsivity from the frequently sampled intravenous glucose tolerance test. Comput Methods Programs Biomed 23(2):113-22.

Reaven G M. 1988. Banting lecture 1988. Role of insulin resistance in human disease. Diabetes 37(12):1595-607.

Sakul H, Pratley R, Cardon L, Ravussin E, Mott D, Bogardus C. 1997. Familiality of physical and metabolic characteristics that predict the development of non-insulin-dependent diabetes mellitus in Pima Indians. Am J Hum Genet 60(3):651-6.

Warram J H, Martin B C, Krolewski A S, Soeldner J S, Kahn C R. 1990. Slow glucose removal rate and hyperinsulinemia precede the development of type II diabetes in the offspring of diabetic parents. Ann Intern Med 113(12):909-15.

Weyer C, Bogardus C, Mott D M, Pratley R E. 1999. The natural history of insulin secretory dysfunction and insulin resistance in the pathogenesis of type 2 diabetes mellitus. J Clin Invest 104(6):787-94.

All publications mentioned herein are incorporated by reference, without limitation, for the purpose of describing and disclosing devices, formulations and methodologies which are described in the publication and which might be used in connection with the presently described methods.

I claim:

1. A method for determining pancreatic β-cell sufficiency in a subject comprising:
   a) administering one or more isotope-labeled sugars to a subject; wherein said one or more isotope-labeled sugars are metabolized to isotope-labeled and/or unlabeled $H_2O$;
   b) obtaining one or more biological samples from said subject before, during or after the administration of said one or more isotope-labeled sugars, wherein at least one biological sample was obtained after the administration of said one or more isotope-labeled sugars;
   c) measuring the isotopic content of $H_2O$ in said one or more biological samples to determine the fractional amount of said isotope-labeled $H_2O$ in said one or more biological samples;
   d) determining the total amount of $H_2O$ in said subject before, during or after the administration of said one or more isotope-labeled sugars;
   e) multiplying said fractional amount of said isotope-labeled $H_2O$ in said one or more biological samples by said total amount of $H_2O$ in said subject to determine the total amount of said isotope-labeled $H_2O$ in said subject to thereby determine pancreatic β-cell sufficiency in said subject.

2. The method of claim 1 wherein said one or more isotope-labeled sugars is selected from the group consisting of isotope-labeled glucose, isotope-labeled fructose, and isotope-labeled galactose.

3. The method of claim 2 wherein said one or more isotope-labeled sugars is isotope-labeled glucose.

4. The method of claim 3 wherein said isotope-labeled glucose selected from the group consisting of [6,6-$^2H_2$]glucose, [1-$^2H$]glucose, and [1,2,3,4,5,6,7-$^2H_7$]glucose.

5. The method of claim 1 wherein said one or more isotope-labeled sugars is administered by a method selected from the group consisting of orally, by gavage, intraperitoneally, intravenously, and subcutaneously.

6. The method of claim 1 wherein said subject is a human.

7. The method of claim 1 wherein said subject is an experimental animal.

8. The method of claim 7 wherein said experimental animal is an animal model of insulin resistance or diabetes.

* * * * *